United States Patent [19]

Gosselink

[11] Patent Number: 4,721,580

[45] Date of Patent: Jan. 26, 1988

[54] ANIONIC END-CAPPED OLIGOMERIC ESTERS AS SOIL RELEASE AGENTS IN DETERGENT COMPOSITIONS

[75] Inventor: Eugene P. Gosselink, Cincinnati, Ohio

[73] Assignee: The Procter & Gamble Company, Cincinnati, Ohio

[21] Appl. No.: 1,137

[22] Filed: Jan. 7, 1987

[51] Int. Cl.$^4$ .................. C07C 143/10; C08G 63/68; D06M 13/30; D06M 15/507

[52] U.S. Cl. .................................. 252/90; 8/115.6; 252/8.7; 252/8.75; 252/92; 252/173; 252/174; 252/538; 252/539; 252/547; 252/548; 252/558; 252/559; 252/DIG. 2; 560/87; 427/242; 427/393.4; 528/293; 528/295

[58] Field of Search ................. 560/87; 528/293, 295; 427/242, 393.4; 8/115.6; 252/8.7, 8.75, 90, 92, 153, 173, 174, 538, 539, 547, 548, 558, 559, DIG. 2, DIG. 14

[56] References Cited

U.S. PATENT DOCUMENTS

| | | | |
|---|---|---|---|
| 3,416,952 | 12/1968 | McIntyre et al. | 117/118 |
| 3,512,920 | 5/1970 | Dunlap | 8/115.7 |
| 3,639,352 | 2/1972 | Katsuura | 528/293 |
| 3,712,873 | 1/1973 | Zenk | 260/29.2 |
| 3,821,169 | 6/1974 | Duddey | 528/293 |
| 3,823,185 | 7/1974 | Schlossman | 260/513 |
| 3,893,929 | 7/1975 | Basadur | 252/8.6 |
| 4,116,885 | 9/1978 | Derstadt et al. | 252/532 |
| 4,132,680 | 2/1979 | Nicol | 252/547 |
| 4,156,073 | 5/1979 | Login | 528/295 |
| 4,161,577 | 7/1979 | Price | 528/295 |
| 4,238,531 | 12/1980 | Rudy et al. | 427/242 |
| 4,427,557 | 1/1984 | Stockburger | 252/8.7 |
| 4,525,524 | 6/1985 | Tung et al. | 524/601 |
| 4,598,141 | 3/1985 | Fock | 528/293 |

FOREIGN PATENT DOCUMENTS

| | | |
|---|---|---|
| 1100262 | 5/1981 | Canada . |
| 185427 | 6/1986 | European Pat. Off. . |
| 194127 | 9/1986 | European Pat. Off. . |
| 199403 | 10/1986 | European Pat. Off. . |
| 47-35311 | 9/1972 | Japan . |
| 47-35312 | 9/1972 | Japan . |
| 1161668 | 8/1969 | United Kingdom ............ 560/87 |
| 2172608 | 9/1986 | United Kingdom . |

OTHER PUBLICATIONS

"Polyesters and their Applications", Bjorksten et al, Reinhold, 1956.
Handbook of Fiber Science and Technology, Marcel Dekker, New York, NY, 1984, vol. II, Part B, Chapter 3, entitled "Soil Release Finishes", (Kissa).
Ponnusamy et al, Makromol. Chem. 184, pp. 1279-1284, 1983.

Primary Examiner—Dennis Albrecht
Attorney, Agent, or Firm—Steven J. Goldstein; Jerry J. Yetter; Richard C. Witte

[57] ABSTRACT

Oligomeric esters and mixtures thereof useful as soil release agents in consumer laundering and fabric care compositions are disclosed. Preferred oligomers have the formulae

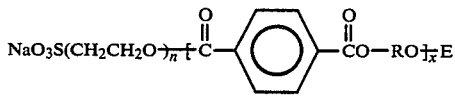

wherein E is

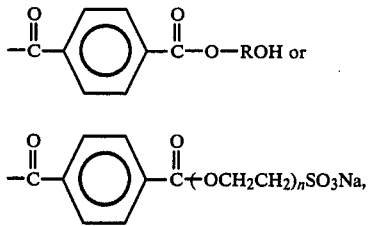

wherein the R substituents may be the same or different and are members selected from the group consisting of —CH$_2$CH(CH$_3$)—, —CH(CH$_3$)CH$_2$— and —CH$_2$CH$_2$—, n is an integer from 1 to 30 and x is an integer from 0 to about 20 provided that when E is

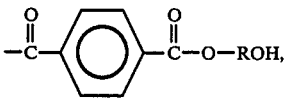

x is at least 1. Mixtures of the oligomers having one and two NaO$_3$S(CH$_2$CH$_2$O)$_n$—substituents are particularly effective and formulable soil release agents in detergent compositions.

18 Claims, No Drawings

ANIONIC END-CAPPED OLIGOMERIC ESTERS AS SOIL RELEASE AGENTS IN DETERGENT COMPOSITIONS

TECHNICAL FIELD

The present invention relates to particular oligomeric esters having anionic capping groups, useful as soil release agents in consumer laundering and fabric care compositions. In their fabric care aspects, modern versions of such compositions address consumer needs in fields which include fabric softening and the provision of antistatic or soil release properties to synthetic fabrics.

BACKGROUND OF THE INVENTION

A substantial proportion of synthetic fabrics now in use are copolymers of ethylene glycol and terephthalic acid, sold under trade names which include Dacron, Fortrel, Kodel and Blue C Polyester. The removal of oily soil and oily stains, which are hydrophobic, from the surfaces of such fabrics which are likewise hydrophobic in character is well recognized to be technically difficult to achieve using laundry compositions of the type most generally accessible to consumers.

It has been recognized in the art that the provision of substances which attach to the surfaces of polyester fabrics and render them more hydrophilic in character is helpful in achieving improved oily soil and oily stain release from such fabrics. Substances which have been used in consumer products as soil release agents are generally copolymers of moderately high (e.g., 40,000 to 50,000) molecular weight, containing ethylene terephthalate segments randomly interspersed with polyethylene glycol segments. See, for example, U.S. Pat. No. 3,962,152, Nicol et al, issued June 8, 1976; a soil release polyester of this type, commercially known as Milease T ®, is further disclosed in U.S. Pat. No. 4,116,885, Derstadt et al, issued Sept. 7, 1978; other commercial variants are Permalose ® and Zelcon ® (see Canadian Pat. No. 1,100,262, Baker et al, issued May 5, 1981 and U.S. Pat. No. 4,238,531, Rudy et al, issued Dec. 9, 1980).

The development of new soil release agents delivering technically outstanding soil release performance cost-effectively in consumer laundering and fabric care compositions is not straightforward. To be particularly useful, efficient adsorption and surface coverage of polyester fabric surfaces by the soil release agent must occur with minimum interference from the product matrix which is being used as a vehicle to convey the soil release agent to the fabric surface. Matrix interferences, when they occur, not only decrease the effectiveness of the soil release agent, but also reduce the cleaning, softening and/or antistatic benefits of other ingredients which may also be present in the product. formulability of the soil release agent is also a major consideration, since the limited solubility and/or dispersibility of art-taught polyesters frequently imposes serious constraints on the range of formulations into which the soil release agent may stably be introduced. Such challenges are generally absent from compositions used in industrial textile treatments, but are well-known to manufacturers of fully-formulated consumer products.

Soil release agents which satisfy these criteria in various consumer laundering and fabric care compositions, particularly home laundry compositions which contain anionic surfactants, would be highly desirable.

It is an object of the present invention to provide novel anionic-capped oligomeric esters having one and two anionic capping groups.

It is a further object to provide compositions for use as soil release agents in consumer laundering and fabric care compositions, said compositions comprising anionic-capped oligomeric esters of the present invention or mixtures thereof.

These and other objects are secured herein, as will be seen from the following disclosure.

BACKGROUND ART

A. Soil Release Finishes

*Handbook of Fiber Science and Technology*, Marcel Dekker, New York, NY, 1984, Volume II, Part B, Chapter 3 entitled "Soil Release Finishes", is a recent review of soil release agents. Almost all of the soil release agents, including anionic soil release agents, reviewed appear to find application principally outside the laundry detergent context, e.g., in industrial textile treatment. The anionic soil release agents reviewed are generally polyacrylates rather than polyesters, and contain ionizable carboxylate groups.

B. Polyester Chemistry

"*Polyesters and their Applications*", Bjorksten et al, Reinhold, 1956, reviews the older and well-established art of polyester synthesis, with particular emphasis on higher molecular weight polyesters used to form fibers or shaped articles.

C. Polyester Backbones

Ponnusamy et al, *Makromol. Chem.* 184, 1279–1284 (1983), discloses a recent synthesis and characterization of copolyesters of ethylene glycol, 1,2-propylene glycol, or mixtures thereof, with dimthyl terephthalate. Molecular weights of the products range from 4000–6000.

D. Capping Reagents and Capped Polyesters

U.S. Pat. No. 3,823,185, Schlossman, issued July 9, 1974, discloses the synthesis of $H(OCH_2CH_2)_nSO_3Z$ (Z=H or Na). Derivatives having n=4, 5 and 9 were isolated. Synthesis route was via ethoxylation of sodium isethionate.

Japanese Patent Documents JP 47/35311 and JP 47/35312, Kobayashi et al, published Sept. 5, 1972, disclose modification of polyester fibers for improved dyeability using poly(ethylene glycol)sulfoethyl ether alkali metal salts, e.g., $HO(CH_2CH_2O)_nCH_2CH_2SO_3M$ (M=Na or K). The molecular weight of the reagent was either 544 or 640.

U.S. Pat. No. 4,525,524, Tung et al, issued June 25, 1985, discloses polyester compositions having an increased affinity for water-based systems. The polyesters incorporate salts of organic sulfonic acid monomers and are carboxyl terminated to a substantial degree.

E. Ethylene terephthalate/PEG terephthalate soil release polyesters used in laundry detergent compositions U.S. Pat. No. 4,116,885, Derstadt et al, issued Sept. 26, 1978, discloses laundry detergent compositions containing 0.15 to 25% (most preferably 0.5 to 10%) of an ethylene terephthalate/PEG terephthalate soil release polyester, such as MILEASE T, having an average molecular weight of 5,000 to 200,000 (preferably 10,000 to 50,000). These detergent compositions further contain 5 to 95% (most preferably 10 to 25%) of certain compatible alcohol sulfate and alkylethoxy sulfate detergent surfactants and no more than 10% of other incompatible anionic surfactants such as the linear alkyl benzene sulfonates.

U.S. Pat. No. 4,132,680, Nicol, issued Jan. 2, 1979, also discloses laundry detergent compositions having soil release properties which contain 2 to 95% (preferably 10 to 60%) of a detergent surfactant and 0.15 to 25% (most preferably 1 to 10%) of an ethylene terephthalate/PEG terephthalate (mole ratio of 65:35 to 80:20) soil release polyester having a molecular weight of 10,000 to 50,000, e.g. MILEASE T. These compositions further comprise 0.05 to 15% (most preferably 0.1 to 5%) of a component which disassociates in aqueous solution to yield quaternary ammonium cations having one to three $C_8$–$C_{24}$ alkyl groups. These cations are taught by Nicol to improve the deposition of the soil release polyester on the laundered fabric. See column 11, lines 14–21.

F. Use of polyesters in rinse-added products to impart soil release properties Canadian Pat. No. 1,100,262, Becker et al, issued May 5, 1981, discloses fabric softener compositions containing 1 to 80% (preferably 5 to 50%) of a fabric-softening agent, such as ditallow dimethyl ammonium chloride, in combination with 0.5 to 25% (preferably 1 to 10%) of certain choline fatty acid esters. These softening compositions preferably include 0.5 to 10% (preferably 1 to 5%) of an ethylene terephthalate/PEG terephthalate soil release polyester, such as PERMALOSE or ZELCON.

U.S. Pat. No. 3,893,929, Basadur, issued July 8, 1975, discloses rinse-added acidic solutions containing a soil release agent made from a dibasic carboxylic acid (preferably terephthalic acid), a polyalkylene glycol (preferably a PEG having a molecular weight of 1,300 to 1,800) and an alkylene glycol (ethylene, propylene or butylene glycol). Preferred soil release agents have a molecular weight of from 3,000 to 5,000. Cationic fabric softeners, such as ditallow dimethyl ammonium chloride, can be included in these compositions, but are not preferred "since they tend to retard the deposition of the soil release agent on the polyester fibers at acidic pH." See column 7, lines 54–59.

U.S. Pat. No. 3,712,873, Zenk, issued Jan. 23, 1973, discloses textile treating compositions applied by spraying or padding which comprise 1 to 5% of a fatty alcohol polyethoxylate and 0.1 to 5% of a soil release polyester of the type disclosed in the Basadur patent. These compositions can additionally contain up to 4% of a quaternary ammonium compound having one $C_{16}$–$C_{22}$ alkyl group. The combination of this quaternary ammonium compound with the polyester is described as improving the soil-release characteristic of the treated fabric. Zenk also states that other quaternary ammonium compounds, such as ditallow dimethyl ammonium chloride, did not give the same superior performance. See column 3, lines 57–61.

G. Use of polyesters in dryer-added products to impart soil release properties U.S. Pat. No. 4,238,531, Rudy et al, issued Dec. 9, 1980, discloses dryer-added products which contain a "distributing agent", such as polyethylene glycol, and an adjuvant (which can be a soil release agent) applied to the fabric. Soil release agents disclosed include polyacrylic resins, polyvinyl alcohol and PERMALOSE TG polyesters (see Example 8).

H. Use of polyesters in fabric or textile treating solutions which are heat cured to impart soil release and/or antistatic properties U.S. Pat. No. 3,512,920, Dunlap, issued May 19, 1970, discloses low molecular weight alkylene glycol/polyalkylene glycol terephthalic acid polyesters which are used in resin treating baths containing starch or cellulose derivatives to impart soil release properties to cotton/polyester fabrics after heat curing. The alkylene glycols which can be used to make these polyesters include ethylene glycol, 1,2-propylene glycol, 1,3-propylene glycol, butylene glycol and mixtures thereof. The polyalkylene glycols which can be used include PEG, polybutylene glycol and mixtures thereof which have an average molecular weight of 200 to 20,000 (preferably 1,000 to 5,000).

U.S. Pat. No. 3,416,952, McIntyre et al, issued Dec. 17, 1968, discloses polyester anti-static agents which can contain a water-solvatable polymeric group such as a polyoxyalkylene group having an average molecular weight of from 300 to 6,000. Preferred polyoxyalkylene groups are the PEG's having an average molecular weight of from 1,000 to 4,000. Treatment is carried out by applying an aqueous dispersion of the polyester in the presence of an anti-oxidant, followed by heating to a temperature above 90° C. to obtain a durable coating of the polyester on the treated article. Example 6 discloses one such polyester formed by the catalyzed reaction of dimethyl terephthalate, ethylene glycol and an O-methyl poly(oxyethylene)glycol having an average molecular weight of 350. A 20% solution of this polyester in benzyl alcohol was used to impart anti-static properties to a polyester fabric. Example 7 discloses a 20% aqueous solution of a similar polyester used to impart anti-static properties to a polyester fabric.

U.S. Pat. No. 4,427,557, Stockburger, issued Jan. 24, 1984, discloses low molecular weight copolyesters (2,000 to 10,000) formed by the reaction of ethylene glycol, a PEG having an average molecular weight of 200 to 1,000, an aromatic dicarboxylic acid (e.g., dimethyl terephthalate), and a sulfonated aromatic dicarboxylic acid (e.g., dimethyl 5-sulfoisophthalate). The PEG can be replaced, in part, with monoalkylethers of PEG such as the methyl, ethyl and butyl ethers. A dispersion or solution of the copolyester is applied to the textile material and then heat set at elevated temperatures (90° to 150° C.) to impart durable soil release properties. See also the McIntyre et al. patent, where Example 2 discloses a random copolyester used to impart antistatic properties which is formed by reacting dimethyl terephthalate, sodium dimethyl sulfoisophthalate, ethylene glycol and a PEG having an average molecular weight of 1540.

SUMMARY OF THE INVENTION

The present invention relates to oligomeric soil-release esters having at least one anionic substituent group, said esters having the formula

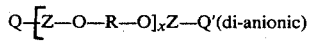

or

[Q''—Z—O—R—O]$_y$H (mono-anionic)     II or mixtures thereof; wherein Q, Q' and Q'' may be the same or different anionic substituents and are members selected from the group consisting of MO$_3$S(CH$_2$CH$_2$O)$_n$—, MO$_3$S—(L)$_q$(YO)$_m$(CH$_2$CH$_2$O)$_r$ and mixtures thereof wherein M is H or a salt-forming cation, L is phenoxyethoxy, phenoxypropoxy or C$_1$–C$_6$ alkoxy, Y is —CH$_2$CH(CH$_3$)— or —CH(CH$_3$)CH$_2$—, n is an integer from 1 to 30, q is 1 or 0, m is an integer from 0 to 15 provided that m+q is at least 1, and r is an integer from 0 to 30; x and y may be the same or different and are each integers ranging from 0 to 20 and from 1 to 20, respectively; the R- substituents of the formulae I and II may be the same or different alkylene substituents selected from the group consisting of —CH$_2$CH$_2$—, —CH$_2$CH(X)— and —CH(X)CH$_2$— wherein X is methyl, ethyl, methoxymethyl, or C$_1$–C$_4$-alkylpoly(oxyalkylene)oxymethyl, or mixtures thereof; and the Z- substituents of the formulae may be the same or different aryldicarbonyl substituents selected from the group consisting of

and mixtures thereof with aryl 1,3-dicarbonyl or substituted aryl-1,3-dicarbonyl or substituted aryl-1,4-dicarbonyl groups.

Particularly preferred are those mono- and di-anionic esters wherein Z is

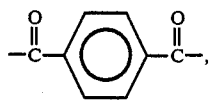

all R substituents are independently selected from —CH$_2$CH$_2$—, —CH$_2$CH(CH$_3$)— and —CH(CH$_3$)CH$_2$—, and Q, Q' and Q'' may be the same or different and are each selected from NaO$_3$S(CH$_2$CH$_2$O)$_n$ wherein is is an integer from 2 to 15, and x and y are integers of from 3 to 7 and from 4 to 8, respectively.

The content of such preferred esters, incorporating from at least four terephthalates to eight terephthalate groups in the molecular structure, is at least 2 weight percent in preferred mixtures of the esters of the invention, the compositions of which are given in more detail hereinafter.

The present invention further relates to consumer laundering and fabric care comprises for use in a pretreatment, through-the-wash, rinse- or tumble-dryer added mode which comprise an effective amount (generally 0.1% to 50%) of a soil release component selected from the herein disclosed anionic oligomeric esters (I and II) and mixtures thereof. The present invention is especially useful in consumer laundering and fabric care compositions which further comprise from about 0.1 to about 99% by weight of a detersive surfactant selected from nonionic, anionic, ampholytic, zwitterionic or cationic detersive surfactants or mixtures thereof. In a heretofore less preferred yet now effective form, the detersive surfactant component of such embodiments is selected from anionic surfactants and mixtures of anionic surfactants with other surfactants as diclosed hereinafter. Embodiments of the invention for use in a rinse or tumble-dryer added mode will generally comprise the hereinabove defined soil release component together with a conventional fabric softening ingredient.

DETAILED DESCRIPTION OF THE INVENTION

The components of the present invention are described in detail below

In general, oligomeric anionic esters and mixtures thereof of the present invention assist the release of oily soils and stains from synthetic fabrics, in particular, from polyester fabrics and polyester/cotton fabric blends to which said esters and mixtures thereof have been attached, or are in the process of being attached by means of a laundering and fabric care composition of the invention. The esters herein are effective at low levels. Importantly, the esters herein can be used in typical consumer products without the consumer having to change standard usage habits and practices. It is expected that the oligomeric esters and mixtures thereof of the invention will also provide whiteness maintenance benefits and will be biodegradable. Single or multiple treatments of synthetic fabrics with the oligomeric esters of the invention provide effective soil release benefits. Particular anionic oligomeric esters of the invention are of special utility in a single-treatment application.

Without intending to be limited by theory, it is believed that the anionic oligomeric esters and mixtures thereof of the invention embody a combination of (a) one, two, or mixtures of one and two, anionic hydrophilic groups directly responsible for covering and protecting the synthetic fabric surface, said groups being particularly compatible with anionic detergent compositions frequently used both as a vehicle to deliver the oligomeric esters to the fabric surface and in subsequent treatments of the fabric with or without further addition of oligomeric esters of the invention; (b) an oligomeric backbone, the structure of which renders the anionic oligomeric esters, substantive to fabric surfaces, especially to synthetic fabric surfaces and most particularly, to fabrics derived from polyester fibers. The structure of said backbone may be modified so that, in combination with the type of anionic group selected, the formulability of the oligomeric esters is maximized.

Further, without intending to be limited by theory, it is to be appreciated that the oligomeric anionic ester mixtures of the invention provide low molecular weight anionic soil release agents, the fabric substantivity of which is maximized through incorporation of particular numbers of terephthalate units in the oligomer backbone. A low degree of symmetry is introduced in the anionic oligomeric esters and mixtures thereof by varying the ratios of ethylene and unsymmetrical 1,2-propylene substituents, by mixing esters having one and two anionic capping groups, and by introduction of varying degrees of ethoxylation in said capping groups. In combination, these symmetry-reducing factors are believed to be associated with the enhanced and wide-ranging formulability and improved soil release effectiveness of the anionic oligomeric ester mixtures of this invention. Furthermore, it is believed that the formulability of the most effective soil-release esters (which contain from about four to about eight fabric-substantive aryldicarbonyl substituents) may actually be enhanced in ester mixtures of the invention by the co-presence therein of esters having less than four aryldicarbonyl substituents in the oligomeric backbone: these may not be optimally fabric substantive, but may be particularly effective solubilizing agents for the preferred anionic oligomeric esters.

All percentages, ratios and proportions disclosed herein are expressed on a weight basis unless otherwise specified.

Oligomeric Esters

The preferred anionic oligomeric soil release esters of the present invention have specific sulfoethoxylated end-caps, and are of the general formulae:

$$Q\text{-}[Z\text{---}O\text{---}R\text{---}O]_x Z\text{---}Q' \text{ (di-anionic esters)} \qquad I$$

or $$Q''\text{-}[Z\text{---}O\text{---}R\text{---}O]_y H \text{ (mono-anionic esters)} \qquad II$$

or are any mixture of esters having formulas I and II.

In these formulae, Q, Q' and Q'' are all capping groups selected from the group consisting of $MO_3S(CH_2CH_2O)_n\text{-}$ wherein n is an integer from 1 to 30 or, more preferably, from 2 to 15 and M is H or a salt-forming cation such as an alkali metal, ammonium, substituted ammonium, or the like.

The composition of the anionic oligomeric esters with respect to groups Q, Q' and Q'' can be modified in four distinct ways:

(a) by selection of $MO_3S(CH_2CH_2O)_n$-containing reagent(s) used in the synthesis;
(b) by physical separation after synthesis;
(c) by mixing or blending after synthesis;
(d) by selecting anionic caps other than $MO_3S(CH_2CH_2O)_{\bar{n}}$ or a proportion of a nonsulfonated polyethoxylate capping reagent.

In the above, modification (a) is preferred; (b) and (c) are less convenient, and (d) is only tolerable provided that the soil release properties and formulability of the oligomeric esters are not adversely affected.

In general, practice of (a) above to arrive at particular combinations of Q, Q' and Q'' groups may involve any of three effective variations:

(i) when each molecule of the $MO_3S(CH_2CH_2O)_{\bar{n}}$-containing reagent used in synthesis has the same, fixed integral value of n, e.g., 3, 6, 9, or 13, then the Q, Q' and Q'' groups of the anionic oligomeric esters will be identical, since all will have the same fixed value of n as in the reagent;

(ii) when the source of $MO_3S(CH_2CH_2O)_{\bar{n}}$ groups is a nonfractionated or commercial ethoxylate having a statistical distribution of n- values, a statistical distribution of values of n will characterize the resulting anionic oligomeric esters. Any individual oligomeric ester molecule will have any of the different, statistically allowed values of n for the different $MO_3S(CH_2CH_2O)_{\bar{n}}$ groups. The anionic oligomeric ester mixtures resulting from the use of such commercial ethoxylates in the syntheses herein will be further characterized in having a mean or average value of n (denoted $\bar{n}$) such that $1 < \bar{n} < 15$. The ethoxylate distributions are expected to be skewed, monomodal distributions resembling those typically obtained in commercial ethoxylation reactions. (See N. Schonfeldt, "Surface Active Ethylene Oxide Adducts", Pergamon, NY, 1969, pp 47–62, for further details on this subject.) It is to be understood that all such compounds having the end-cap ethoxylation variations noted are useful in the practice of this invention. For cost reasons it is generally preferred to use nonfractionated commercial reagents in their synthesis;

(iii) when the source of $MO_3S(CH_2CH_2O)_n$-groups is a mixture of one or more $MO_3S(CH_2CH_2O)_n$-containing reagents having different values of n, then the Q, Q' and Q'' groups of the resulting anionic oligomeric ester mixture will have any of the values of n allowed by the reagent mixture, the proportions being governed by the composition of the reagent mixtures.

The anionic capping groups of the oligomeric esters contain a substituent M which in any individual oligomeric ester molecule may be H or a salt-forming cation. It should be recognized that, through their tendency to promote hydrolysis, high concentrations of acidic esters or acidic capping reagents can undesirably affect the stability of the oligomeric esters of the invention. For this reason, the oligomeric esters of most practical importance in the present invention will generally have primarily M=Na rather than M=H substitution. Most generally as prepared, however, M in each anionic oligomeric ester molecule will be selected from H, Na and mixtures thereof, and the relative proportions of these substituents in the overall ester compositions and their degree of dissociation will depend upon the pH and concentration of the aqueous phase associated with solutions, oils or slurries made by mixing the esters with varying amounts of water, aqueous acid, aqueous alkali, or detersive ingredients more fully described below. When the esters have not been treated with water, the identity and proportions of M substituents will depend exclusively upon the proportion of different M substituents present in the $MO_3S(CH_2CH_2O)_n$-containing reagents used in the synthesis of the esters. In contrast, esters placed in water containing salt-forming cations such as $Ca^{2+}$, $Mg^{2+}$ or the like will generally undergo ion exchange with such cations, displacing $Na^+$. It is, of course, understood and appreciated that in defining the esters of the present invention it is intended to include both the commercially accessible ethoxylate mixtures and the commercially accessible acid or salt forms of the esters, or mixtures thereof, as well as the salt forms which may result by formulating the oligomeric esters into commercial products or otherwise by exposing said esters to aqueous baths containing salt-forming cations.

Alternative, effective anionic soil release esters of the present invention have anionic capping groups Q, Q' and Q'' which are the same or different and are selected from groups $MO_2S\text{-}(L)_q(YO)_m(CH_2CH_2O)_r$-wherein M is H or a salt-forming cation, L is phenoxyethoxy, phenoxypropoxy or $C_1$-$C_6$ alkoxy, Y is $-CH_2CH(CH_3)-$ or $-CH(CH_3)CH_2-$, q is 1 or 0, m is an integer from 0 to 15 provided that $m+q$ is at least 1, and r is an integer from 0 to 30. Mixtures of these alternatively capped esters with the hereinbefore defined $MO_3S(CH_2C\text{-}H_2O)_r$-capped esters are likewise effective soil release agents. The alternatively capped esters are, however, generally less preferred than the exclusively $MO_3S(CH_2CH_2O)_n$-capped esters on grounds of increased cost.

The oligomeric backbones of the anionic esters of the invention comprise $-[Z-O-R-O]-$ moieties, wherein the Z-substituents may be the same or different aryldicarbonyl substituents which are independently selected from the group consisting of

and mixtures thereof with aryl-1,3-dicarbonyl, substituted aryl-1,3-dicarbonyl or substituted aryl-1,4-dicarbonyl groups, and the R-substituents may be the same or different alkylene substituents selected from the group consisting of —CH$_2$CH$_2$—, —CH$_2$CH(X)— and —CH(X)CH$_2$— wherein X is methyl, ethyl, methoxymethyl or C$_1$-C$_4$-alkylpoly(oxyalkylene)oxymethyl, or mixtures thereof. Preferred oligomeric backbones contain

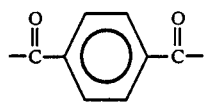

as Z-substituents and exclusively ethylene, 1,2-propylene or mixtures thereof as R-substituents. Esters having at least 0.1 mole fraction of —CH$_2$CH(CH$_3$)— and —CH(CH$_3$)CH$_2$— substituents, when the total number of moles of R substituents is taken to be 1.0, are highly preferred; the unsymmetrically placed methyl group in these 1,2-propylene substituents may (without intending to be limited by theory) have desirable effects on formulability and thereby also on soil-release effectiveness. The $\{Z-O-R-O\}$ moieties may be randomly connected as in the illustrative partial formula A:

A: $\{Z'-O-R^a-O\}\{Z^2-O-R^b-O\}\{Z^2-O-R^c-O\}\{Z^2-O-R^b-O\}$ wherein Z$^1$, Z$^2$ and Z$^3$ are all

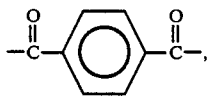

R$^a$ is

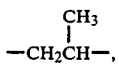
—CH$_2$CH—,

R$^b$ is

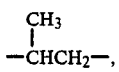
—CHCH$_2$—, and R$^c$ is —CH$_2$CH$_2$—. Alternatively, the $\{Z-O-R-O\}$ moieties may be connected in "blocks" such as in the illustrative formula B:

B: $\{Z'-O-R^a-O\}_i\{Z'-O-R^c-O\}_j$ wherein Z' is

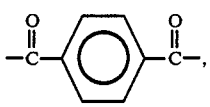

R$^a$ is

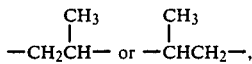

and R$^c$ is —CH$_2$CH$_2$—. Formula B indicates empirically a degree of polymerization i with respect to inclusion of 1,2-propylene-derived moieties and a degree of polymerization j with respect to inclusion of ethylene-derived $\{Z-O-R-O\}$ moieties. The numbers represented by i and j, used illustratively here, are directly determined by the mole fractions of the alkylene substituents. Formula B, illustrating the oligomeric backbones of certain anionic esters of the invention, is not necessarily restricted to backbones having only two distinct blocks; the representation includes both such a symmetrical derivative and derivatives with progressively higher randomness of structure, ultimately also including essentially random oligomers.

Most generally, no attempt is made to arrive at a particular degree of order in the oligomeric backbone. However, by adjusting parameters such as the time, temperature and proportions of particular oligomeric reactants and sequence of addition in the syntheses described more fully below, the ordering of $\{Z-O-R-O\}$ units in the backbones of the oligomeric esters could be influenced, with potential advantage for the formulability and use of the oligomeric esters as soil release agents. In any event, and irrespective of the possible variations noted, the anionic oligomeric esters of the present invention exhibit improved soil release properties, as will be seen from the disclosures, hereinafter.

The oligomeric backbones of formulae I and II indicate the overall degree of oligomerization of said backbones by integers x and y respectively. Integers x and y may be the same or different, x being selected from 0 to about 20 and y being selected from 1 to about 20. Oligomeric esters with individual integer values of x and y may be fractionated using techniques described more fully below. Mixtures of esters which are inherently the result of the synthetic procedure used are preferred for cost-effectiveness and formulability and will generally be further characterized in having a particular, not necessarily integral, average degree of polymerization. It is believed that under such circumstances this average degree of polymerization will be about the same for both mono- and di-anionic esters copresent in these mixtures which are the direct result of the synthetic procedure (y will not be independent of x). The average degree of polymerization denoted $\bar{x}$ will then be in the range $0.3 \leq \bar{x} \leq 7$. At the molecular level, the y values in structure II will then generally coincide with x+1. However, blended compositions may be prepared in which x and y are not necessarily related variables.

Particularly preferred mono- and di-anionic esters of the invention are those wherein Z is

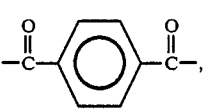

all R substituents are independently selected from —CH$_2$CH$_2$—, —CH$_2$CH(CH$_3$)— and —CH(CH$_3$)CH$_2$—, Q, Q' and Q" may be the same or different and are each selected from NaO$_3$S(CH$_2$CH$_2$O)$_{\overline{n}}$ wherein n is an integer from 2 to 15, and x and y are integers of from 3 to 7 and from 4 to 8, respectively. The selection of M=Na in such preferred ester compositions is associated with the lower cost and environmental acceptability of this salt-forming cation.

Highly preferred mixtures of mono- and di-anionic esters of the invention comprise at least 2 weight percent of the preferred $NaO_3S(CH_2CH_2O)_{\overline{n}}$-capped esters having four to eight terephthalate substituents, together with esters of otherwise identically defined molecular structures but containing less than four, or more than eight terephthalate units. As hereinbefore indicated, the lower molecular weight component of the latter esters is considered unlikely to be optimally fabric-substantive but may be particularly effective in solubilizing the preferred anionic oligomeric esters. While not intending to be limited by theory, this may indirectly enhance the formulability and soil-release effectiveness of the preferred oligomeric esters.

The weight ratio of oligomeric esters having structure I (di-anionic) and structure II (mono-anionic) in preferred mixtures of mono- and di-anionic esters of the invention will generally be between about 30:1 and about 1:20 in preferred ester mixtures; control of such ratios is taught in the synthetic methods herein.

Esters having more than eight terephthalate units are also believed to have soil release effectiveness, but are anticipated to have reduced solubility and formulability with increasing molecular weight. Without intending to be limited by theory, it is believed that the solubilizing function of esters having less than four aryldicarbonyl substituents may nonetheless improve the formulability of the higher molecular weight ester component in mixtures of esters herein. Irrespective of theory, the ester mixtures herein are effective for the purposes of practicing the invention, and will generally have average molecular weights below 4000, more preferably, below 3000.

METHOD FOR MAKING THE OLIGOMERIC ESTERS

The oligomeric esters of the present invention can be prepared by a combination of art-recognized methods. Although the following synthesis description is for the preferred oligomeric esters of the present invention, other versions can be prepared by appropriate variation.

The sulfonated oligomeric esters of the present invention are typically formed from (1) ethylene glycol, 1,2-propylene glycol or a mixture thereof; (2) a compound or mixture of compounds of the formula $NaO_3S(CH_2CH_2O)_nH$ wherein n is as disclosed above; and (3) a dicarboxylic acid or its diester, dimethyl terephthalate being preferred. The respective amounts of these three component reagents are selected to prepare oligomeric esters having the desired properties in terms of formulability and soil release properties.

Component reagents $NaO_3S(CH_2CH_2O)_nH$ may be prepared by use of the method reported in the examples hereinafter; it is anticipated that an alternative method of U.S. Pat. No. 3,823,185, Schlossman, issued July 9, 1974, and incorporated herein by reference, may equally be applicable.

Preferably, the only dicarboxylic acid derivative used is terephthalic acid or its diesters; the dimethyl ester is preferred. However, minor amounts of other aromatic dicarboxylic acids (or their diesters), or aliphatic dicarboxylic acids (or their diesters) can be included to the extent that the soil release properties are substantially maintained. Illustrative examples of other aromatic dicarboxylic acids which can be optionally used include isophthalic acid, phthalic acid, naphthalene-, anthracene- and biphenyldicarboxylic acids, as well as their dialkyl esters and mixtures of these acids. If aliphatic dicarboxylic acids are included, adipic, pimelic, azelaic, sebacic, suberic, 1,4-cyclohexanedicarboxylic and dodecanedioic acids can be used.

The preferred method for preparing the oligomeric esters of the present invention comprises (a) transesterification (also known as ester interchange reaction) of the mixed component reagents in selected proportions and (b) polymerization of the resultant low molecular weight oligomers to the desired degree (but invariably avoiding the formation of high polymers), this step being carried out either in the originally used reaction vessel, or in a separate apparatus such as a Kugelrohr. A general reaction sequence is indicated in FIG. 1.

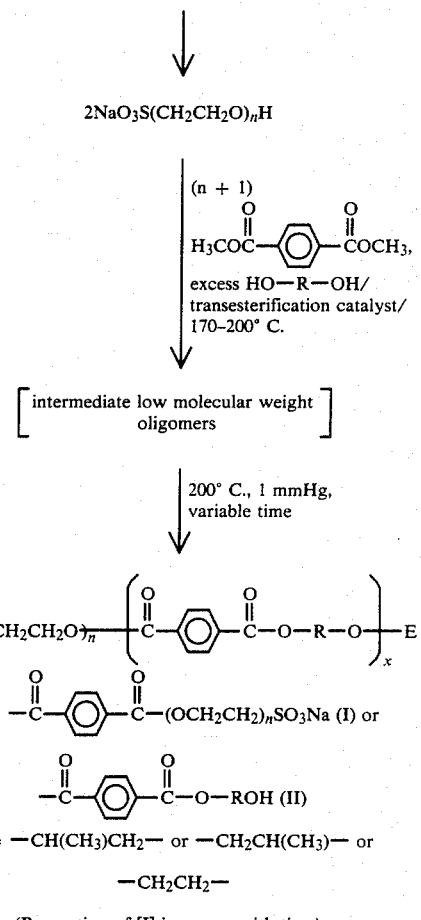

FIG. 1. General Reaction Sequence (Proportion of [I] increases with time)

Whereas the reaction sequence of FIG. 1 indicates that all reagents involved in the transesterification step are ultimately mixed together, it is not intended to exclude modifications of the process wherein the $NaO_3S(CH_2CH_2O)_nH$ reagent is added to a preformed mixture of low-molecular-weight oligomers derived from a separate transesterification of glycols with dicarboxylic acid derivatives. Indeed such process variation may be commercially advantageous.

Irrespective of whether conducted in one or in two stages, the ester interchange reaction herein can be conducted in accordance with reaction conditions typically used for ester interchange reactions: such reactions are usually conducted at temperatures from 120° to 220° C. in the presence of an esterification catalyst, desirably with exclusion of air from the reaction vessel and with agitation. Water or monohydric alcohols (depending on whether dicarboxylic acids or their esters are used) are formed and are constantly removed, thus forcing the reaction to completion. The temperature and pressure of the reaction are desirably controlled (until most of the calculated monohydric alcohol or water has been removed) so that glycol does not distill from the reaction mixture. Higher temperatures can be used if the reaction is conducted under pressure, particularly if fast throughput is allowed by the reactor design. However, generally (at least in small-scale preparations) higher temperatures are not preferred.

The catalysts commonly used for the ester interchange reaction are those known in the art. These catalysts include metals such as zinc, titanium, antimony and tin, usually as their oxides, carbonates or acetates, but desirably as their alkyls or alkyl esters such as, for example, occur in the form of tetraisopropoxytitanium (IV) or n-butyltrihydroxytin(IV). The latter catalyst is commercially available as FASCAT 4100 ® (M&T Chemicals Inc.).

The extent of the ester interchange reaction can be monitored by the amount of alcohol liberated or by the disappearance of the lower alkyl esters of the dibasic acids in the reaction mixture as determined by high pressure liquid chromatography (HPLC), nuclear magnetic resonance spectroscopy (NMR) or other suitable analytical methods. The ester interchange reaction is desirably taken to more than 80% completion; 90-95% completion is preferred.

If desired, stabilizers such as phosphorus derivatives (e.g., phosphoric acid and esters thereof) can be added at the end of the ester interchange step. The purpose of the stabilizer is to inhibit degradation, oxidation, and other side reactions, and/or to destroy the catalytic activity of the ester interchange catalyst. Typically, however, stabilizers need not be used to make the oligomeric esters of the present invention.

When the ester interchange reaction has been carried out, the glycol ester oligomers are further polymerized to increase their molecular weight. Achievement of the desired degree of oligomerization can be monitored by HPLC and NMR analysis. For commercial purposes, the polymerization is usually carried out at temperatures from about 180° to about 260° C. in the presence of a catalyst of the type also used in the ester interchange reaction (illustrative examples of which have been given above).

Excess glycol and other volatiles liberated during the reaction are removed under vacuum, desirably assisted by means of agitation. In small scale preparations, the well-known Kugelrohr apparatus may desirably be used in the polymerization step. The reaction is continued until the desired level of polymerization, as monitored by $^{13}$C NMR and/or reverse phase HPLC and/or gel phase permeation chromatography, is achieved. Final molecular weights of 1000 to 3000 are most preferred. In addition to the oligomeric esters having two anionic capping groups, the crude compositions obtained after synthesis generally also contain oligomeric esters having only one anionic capping group. By simply using longer or shorter reaction times, the proportion of dianionic esters (formula I) or monoanionic esters (formula II) may be varied. Without intending to be limited by theory, ester mixtures comprising at least 0.5 (mole fraction) of formula I esters may be preferred on grounds of soil release effectiveness though not necessarily of cost (longer reaction times). By adjusting the reactant ratios or addition sequences and time, mixtures which also contain a component being exclusively alkylene glycol-terminated ester oligomers can also be obtained. Crude compositions may also contain starting reactants and impurities, byproducts or catalyst residues.

Mixtures prepared in the foregoing manner are generally used in the consumer products disclosed herein. However, purified samples of the individual oligomeric esters sufficient for small-scale testing and evaluation as soil release agents are generally separable from the crude compositions by means of analytical techniques such as HPLC discussed hereinafter more fully. Likewise useable in small-scale testing are blended mixtures of esters derived from separated fractions of the analytically separable esters.

The following Examples further illustrate the anionic oligomers of this invention and their synthesis.

EXAMPLE I

A preferred oligomeric ester made from dimethyl terephthalate, 1,2-propylene glycol and sodium 3,6-dioxa-8-hydroxyoctanesulfonate was synthesized as follows:

A. Preparation of sodium 3,6-dioxa-8-hydroxyoctanesulfonate

Into a 2 l, three-necked round bottom flask, fitted with a magnetic stirrer and condenser, were placed sodium sulfite (214.2 g; 1.7 moles; anhydrous; Fischer) and 800 ml of distilled water. The solution was heated to 60° with agitation to dissolve the $Na_2SO_3$. 2-[2-(2-chloroethoxy)ethoxy]ethanol (236 g; 1.4 moles; 99+% Aldrich) was added under an argon blanket. The solution was heated to 100° C. for 45 hours, under argon, after which time the reaction was demonstrably complete since 2-[2-(2-chloroethoxy)ethoxy]ethanol was absent from the thin layer chromatogram. Water was removed using a rotary evaporator at 60° C. The resulting viscous white oil was extracted for 72 hours in 1.5 l dichloromethane using mechanical stirring of the two-phase mixture. The dichloromethane solution was then filtered, the filtrate dried using anhydrous sodium sulfate and the dichloromethane was removed using a rotary evaporator at 60° C. to yield a colorless, viscous oil, 3,6-dioxa-8-hydroxyoctanesulfonate (309.5 g; 99% yield).

B. Ester interchange and oligomerization

Into a 500 ml, three-necked, round bottom flask, fitted with a magnetic stirrer and a modified Claisen head supporting a condenser and receiving flask were placed sodium 3,6-dioxa-8-hydroxyoctanesulfonate (150 g; 0.67 moles), dimethyl terephthalate (178.6 g; 0.92 moles; Aldrich) and 1,2-propylene glycol (89.7 g; 1.18 moles; Mallinckrodt or Fischer). FASCAT 4100 ® (0.7 g, 0.2% w/w, M&T Chemicals Inc.) was added under an argon blanket. The mixture was heated with agitation under argon over four hours to 175° C. and the temperature, agitation and inert atmosphere were then maintained for 19 hours, during which methanol (86.1 g; 95% of theory) distilled from the reaction vessel. The temperature was raised to 200° C. over a five hour period and the mixture maintained at this temperature for an additional four hours, during which methanol (61.8 g; 105% of theory) containing some 1,2-propylene glycol distilled from the reaction. The apparatus was then cooled to ambient temperature and the reaction mixture was transferred to a Kugelrohr apparatus. The Kugelrohr was maintained under vacuum (ca. 1 mm Hg) and the temperature was raised to 200° C. over a one-hour period. The reaction mixture was held at this temperature for a total of 6.5 hours, at which time 270 MHz $^{13}$C NMR spectroscopy demonstrated the reaction to be complete: the terminal alcohol-bearing carbon atom resonance ($\delta=60.2$ ppm, reference=39.5 ppm) due to 3,6-dioxa-8-hydroxyoctanesulfonate was almost undetectable; also nearly absent was the propylene glycol methyl carbon resonance due to the glycol-terminated oligomer intermediate ($\delta=19.9$ ppm, reference as above). As used herein and throughout the specification, $^{13}$C NMR shifts in parts per million (ppm) are referred to tetramethylsilane (0 ppm) using dimethylsulfoxide (39.5 ppm) as secondary reference for convenience. The remaining resonances of the $^{13}$C NMR spectrum were consistent with the formation of sulfoethoxylated poly(propylene terephthalate)oligomer.

The composition of the product was demonstrated on the basis of $^{1}$H NMR to be given by

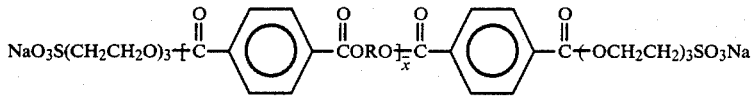

wherein R is

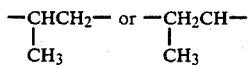

and the average backbone length $\bar{x}$ is 1.75. This oligomeric ester has the dianionic structure I; both on the basis of $^{1}$H and $^{13}$C NMR, a negligible proportion of ester having structure II was present.

EXAMPLE II

A preferred oligomeric ester mixture having copresent esters of structures I and II may be prepared by following the method of Example I with the single modification of stopping the ester oligomerization reaction earlier than the 6.5 hours indicated above (This particular reaction should as above be carried out in the Kugelrohr after ester interchange). The reaction product then includes not only the structure I ester indicated above, but also of a structure II ester; the overall formula of the product is given by

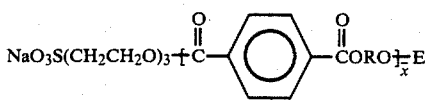

wherein

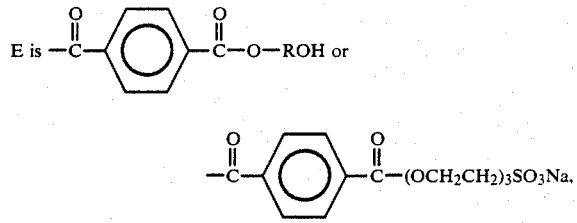

R is as indicated in Example I above, and the average backbone length $\bar{x}$ characterizing the overall mixture of esters lies between 0.3 and 1.75 depending on the precise length of time selected for the oligomerization reaction.

EXAMPLE III

A preferred oligomeric ester mixture made from dimethyl terephthalate, a 33:67 mole percent mixture of ethylene glycol and 1,2-propylene glycol and sodium 3,6-dioxa-8-hydroxyoctanesulfonate was synthesized (using sodium 3,6-dioxa-8-hydroxyoctanesulfonate prepared according to the method [A] of Example I) as follows:

Ester interchange and oligomerization

Into a 500 ml, three-necked, round bottom flask, fitted with a magnetic stirrer and a modified Claisen head supporting a condenser and receiving flask were placed sodium 3,6-dioxa-8-hydroxyoctanesulfonate, (22.4 g, 0.10 moles) dimethyl terephthalate (46.6 g; 0.24 moles; Aldrich), ethylene glycol (7.4 g.; 0.12 moles) and 1,2-propylene glycol (20.1 g; 0.25 moles; Fischer). FASCAT 4100 ® (0.2 g, 0.2% w/w, M&T Chemicals Inc.) was added under an argon blanket. The mixture was heated with agitation under argon over 1.5 hours to 175° C. and the temperature, agitation and inert atmosphere were then maintained for 16 hours, during which methanol (16 g; 104% of theory) containing some ethylene glycol and 1,2-propylene glycol distilled from the reaction. The apparatus was then cooled to ambient temperature and the reaction mixture was transferred to a Kugelrohr apparatus. The Kugelrohr was maintained under vacuum (ca. 1 mm Hg) and the temperature was raised to 200° C. over a 1.5-hour period. The reaction mixture was held at this temperature for a total of 4.5 hours, at which time 270 MHz $^{13}$C NMR spectroscopy demonstrated the reaction to be complete: the terminal alcohol-bearing carbon atom resonance ($\delta=60$ ppm, reference=39.5 ppm) due to 3,6-dioxa-8-hydroxyoctanesulfonate was almost undetectable; also nearly absent was the propylene glycol methyl carbon resonance due to the glycol-terminated oligomer intermediate ($\delta=19$ ppm, reference as above). The remaining resonances of the $^{13}$C NMR spectrum were consistent with the formation of sulfoethoxylated oligomeric ester having an ethylene/propylene "hybrid" backbone, the empirical composition of which was determined in the light of reagent stoichimetry on the basis of NMR as consistent with formation of dianionic esters (structure I) given by B. Ester interchange and oligomerization

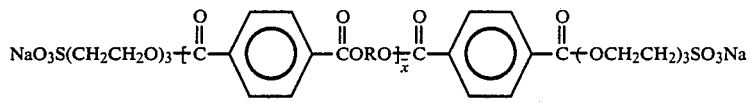

wherein R is —CH$_2$CH$_2$— (approximately 0.33 mole fraction) and

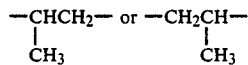

(approximately 0.67 mole fraction) and the average backbone length $\bar{x}$ is approximately 1.75.

EXAMPLE IV

A. Synthesis of a sulfopoly(ethoxy)ethanol, α-(2-sulfoethyl)-ω-hydoxy-poly(oxy-1,2-ethanediyl) NaO$_3$S(CH$_2$CH$_2$O)$_{\bar{n}}$H (i) Ethoxylation of 2-[2-(2-chloroethoxy)ethoxy]ethanol 2-[2-(2-chloroethoxy)ethoxy]ethanol (100 g, 0.59 mole, 99+%, Aldrich) was placed in a preweighed 1 liter, 3-necked round-bottom flask equipped with ethylene oxide gas inlet, argon inlet, gas outlet, magnetic stirrer, internal thermometer and air cooling. The system was flushed with argon and neat boron trifluoride monoetherate (about 0.5 ml, pure, Aldrich) was added. Ethylene oxide gas (Matheson) was passed in with stirring at a rate sufficient to maintain the temperature in the 30°-40° C. range. The addition of ethylene oxide was continued until the weight had increased by 76.5 g (1.74 moles ethylene oxide) to give Cl(CH$_2$CH$_2$O)$_{\bar{n}}$H (176.5 g, 0.59 moles;) with an average degree of ethoxylation $\bar{n}$=5.9 on the basis of weight gain, further confirmed by $^1$H NMR analysis of sulfonated derivative prepared according to (ii) below.

(ii) Reaction with sodium sulfite

Ethoxylated 2-[2-(2-chloroethoxy)ethoxy]ethanol prepared according to (i) (100 g; 0.33 moles) was placed in 150 ml of water with sodium sulfite (50 g; 0.4 moles; anhydrous, Fischer). The system was refluxed for about 40 hours. Water was stripped from the reaction mixture using a rotary evaporator at 20° C. followed by Kugelrohr treatment at 100° C. under a vacuum of 1 mm Hg. The residue was extracted with dichloromethane (500 ml). The resulting supernatant solution was separated and stripped of solvent under reduced pressure to yield NaO$_3$S(CH$_2$CH$_2$O)$_{\bar{n}}$H (102.5 g; 0.28 moles; 85% yield) with an average degree of ethoxylation $\bar{n}$=5.9. $^1$H NMR integrals of —CH$_2$— resonances proximate to NaO$_3$S— in ratio to —CH$_2$— resonances proximate to —O— confirmed the degree of ethoxylation.

More highly ethoxylated homologs may be prepared by increasing the amount of ethylene oxide added during the ethoxylation (step [i]). Such reactions may be conducted in a pressure vessel.

Into a 500 ml, three-necked, round bottom flask, fitted with a magnetic stirrer and a modified Claisen head supporting a condenser and receiving flask were placed NaO$_3$S(CH$_2$CH$_2$O)$_{\bar{n}}$H ($\bar{n}$=5.9) (50 g, 0.14 moles), dimethyl terephthalate (37.0 g; 0.19 moles; Aldrich), and 1,2-propylene glycol (18.6 g; 0.24 moles; Fischer). FASCAT 4100® (0.2 g, 0.2% w/w, M&T Chemicals Inc.) was added under an argon blanket. The mixture was heated with agitation under argon over 2 hours to 175° C. and the temperature, agitation and inert atmosphere were then maintained for 17.5 hours, during which methanol (11.9 g; 98% of theory) distilled from the reaction vessel. The temperature was raised to 200° C. over a 2 hour period and the mixture maintained at this temperature for an additional 5 hours, during which further distillation occurred of methanol (0.9 g; 7% of theory) contaminated with some 1,2-propylene glycol from the reaction. The apparatus was then cooled to ambient temperature and the reaction mixture was transferred to a Kugelrohr apparatus. The Kugelrohr was maintained under a running vacuum (ca 1 mm Hg) and the temperature was raised to 200° C. over a 1.5-hour period. The reaction mixture was held at this temperature for a total of 4 hours, at which time 270 MHz $^{13}$C NMR spectroscopy demonstrated the reaction to be complete: the terminal alcohol-bearing carbon atom resonance (δ=60 ppm, reference=39.5 ppm) due to NaO$_3$S(CH$_2$CH$_2$O)$_{\bar{n}}$H was almost undetectable; also nearly absent was the 1,2 propylene glycol methyl carbon resonance due to the glycol-terminated oligomer intermediate (δ=19 ppm, reference as above). The remaining resonances of the $^{13}$C NMR spectrum were consistent with the formation of

wherein R is

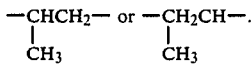

Methods both for Separation and Analysis of Anionic Oligomeric Esters by HPLC Fractionation The crude oligomeric ester compositions of the present invention, such as those of Examples I–IV, can be separated into various, identifiable fractions by high performance, high pressure, liquid chromatography (HPLC). Typically, a chromatogram for identifying and separating the various fractions of the crude oligomeric ester composition is developed using an HPLC apparatus consisting of a sample injection system, a pumping system capable of forming a binary gradient, and an ultraviolet spectrophotometer detector which is connected to a means of recording the detector output.

A typical system providing these capabilities is given as follows:
1. Equipment:
   a. Waters WISP 710B automatic injector
   b. Two Laboratory Data Control (LDC) Model III pumps
   c. LDC Gradient Master
   d. LDC Spectromonitor III detector or more preferably a variable-wavelength detector such as the Spectra Physics Model 8440XR.
   e. Waters Data Module Model 730 recorder
2. Solvent Program:
   a. a linear binary gradient adjusted for optimum performance in function of particular sample; solvents selected from mixtures of water with acetonitrile or methanol. To the water component of the solvent system should be added an ion suppression agent such as sodium acetate, at a concentration of typically 0.01M.
   b. flow rate: typically 1 ml/min
3. Column: 4.6 mm×25 cm. typically Phase Separations Corp. Spherisorb ® 5 micron hexyl or octyl
4. Injection Volume: 10-50 μl
5. Detection: 254 nm uv (fixed wavelength detector) or preferably 245 mm obtainable using the variable-wavelength detector.
6. Sample Preparation: 1.0-4.0 mg/ml predissolved in solvent mixture selected in 2 a. above will generally be preferred for best identification of component esters; however, concentrations up to ca. 50 mg/ml will more conveniently be used in preparative scale separations.

Methods for Analysis of Anionic Oligomeric Esters by $^{13}C$ NMR Spectroscopy $^{13}C$-NMR Analysis The various fractions obtained by HPLC can be analyzed by $^{13}C$-NMR to determine the degree of polymerization of the backbones of oligomeric esters present in each fraction. A $^{13}C$-NMR spectrum of an oligomeric ester composition made similar to Example I has resonances tabulated below. Assignment of carbon resonances are made by comparison to model compounds and/or spiking experiments. $^{13}C$-NMR parameters are chosen to give quantitative information, i.e., peak areas can be used to determine relative levels of intermediate compounds and anionic oligomeric esters present in the semi-preparative HPLC fraction.

Chemical shift assignments of several key carbon resonances are as follows:

| Carbon Resonance | Chemical Shift (ppm) |
|---|---|
| $-CH_2-$ adjacent to $NaO_3S-$ | 51.1 |
| 2,3,5,6 Carbons of Terephthalate | 128.4 |
| 1,4 Carbons of Terephthalate | 132.2-133.0 |
| Carbons of propylene | 16.1 <br> 66.0 } * <br> 69.0 |

*Disappearance of additional peaks in this region of the spectrum, particularly at 19.0 ppm, due to intermediates, is a feature conveniently monitored during the preparation.

Consumer Laundering and Fabric Care Compositions; Detergent Compositions

The anionic oligomeric esters of the present invention are particularly useful in consumer laundering and fabric care compositions to provide soil release properties. The term "consumer laundering and fabric care compositions" are used herein refers to a more broadly defined group of products for textile treatment by individual and institutional consumers than is generally associated with the term "detergent compositions". In recent years, individual and institutional consumers have both expressed a desire for, and have been offered, a rapidly broadening group of products, herein referred to as "consumer laundering and fabric care compositions", which perform functions selected from those individually associated with laundry detergents, rinse-added fabric softeners, tumble-dryer fabric softeners, combined laundry detergent and antistatic fabric treatments, combined laundry detergent and fabric softeners, special-function laundry detergent pretreatments, and the like. Such "consumer laundering and fabric care compositions" provide a group of products which may be exclusively devoted to laundering (i.e., detergent compositions), to fabric care (i.e., rinsed-added fabric softeners and the like), or to combinations of laundering and fabric care attributes; it is the latter group which has most recently shown significant expansion in the marketplace. The oligomeric esters of the present invention are indeed expected to be applicable to fabrics using processes and equipment, as well as controlling means, which are characteristic of laboratory or industrial textile treatment environments (e.g., through padding processes and equipment and the associated controlled environment in terms of pressure, temperature, concentration, time and the like); however, it is to the challenge of providing both soil release effectiveness and wide-ranging formulability and matrix compatibility that the oligomeric esters of the invention are particularly directed. Consumer laundering and fabric care compositions cover a wide range of formulations and are used for fabric treatment in quite variable and frequently poorly controlled ways by institutional or consumer end-users who have access only to washing machines, tumble dryers and the like, which are in reality primitive devices when compared with industrial or laboratory process equipment. To be commercially viable in this context, truly effective soil release agents should be conveyable to textile surfaces by means of diverse product formulations of widely ranging form, and function to deliver a standardized and cost-optimized soil release benefit to consumers by means of whatsoever convenient matrix they may prefer.

Modern consumer laundering and fabric care compositions currently being introduced to consumers include multi-functional assemblies of discrete or mixed laundry detergent and/or fabric care ingredients releasably contained in a series of pouches or the like. Such assemblies may also use coatings, microencapsulation or the like to keep particular laundry detergent and/or fabric care ingredients separated from one another during product storage. Effective consumer laundering and fabric care compositions making use of pouch, coating or microencapsulation containment of oligomeric esters of the invention may be envisioned. The concentration of the esters contained within such pouches, coatings or microcapsules may vary widely.

Soil Release Component

Any consumer laundering and fabric care composition of the invention, be it in a traditional granular or liquid laundry detergent form, or be it in a less conventional form such as a pouch or a sheet composition, comprises a soil release component which contains an effective amount of the anionic soil release oligomeric esters previously defined. What is an "effective amount" will depend upon the particular oligomeric esters used, the form of the consumer laundering and fabric care composition (liquid, granule, pouch, tablet, etc.) and the magnitude and type of benefits desired (e.g., pretreatment of clean fabrics to subsequently provide soil release; simultaneous cleaning and soil release treatment and the like). In detergent compositions which are in liquid or granular forms, the anionic oligomeric esters of the invention are generally effective at levels of from about 0.01 to about 10% by weight of the composition. In terms of soil release benefits, preferred detergent compositions can comprise from about 0.1 to about 5% by weight of the soil release esters; typically, from about 0.1 to about 3% by weight of these esters. In contrast, pouch additive or encapsulated compositions in which oligomeric esters of the invention are releasably contained may have locally high concentrations, from about 0.01 to about 95% by weight, of the esters and yet provide equally effective concentrations of the soil release esters when compared with those yielded to a washing machine or tumble dryer by a more conventional formulation means with differing dosage level.

Detersive Surfactant

The amount of detersive surfactant included in the detergent compositions of the present invention can vary from about 1% to about 99% by weight of the composition depending upon the particular surfactant(s) used, the form of composition to be formulated (e.g., granule, liquid, liquid concentrate, sheet, pouch) and the effects desired. Preferably, the detersive surfactant(s) comprises from about 5% to about 80% by weight of the composition. The detersive surfactant can be nonionic, anionic, ampholytic, zwitterionic, or cationic. Mixtures of these surfactants can also be used. Preferred detergent compositions of the present invention combine the cost-effectiveness of anionic surfactants with the increased compatibility of the anionic oligomeric esters of the invention with such surfactants. Preferred detergent compositions, therefore, comprise anionic detersive surfactants or mixtures of anionic surfactants with other surfactants disclosed herein, together with the oligomeric esters of the invention.

A. Nonionic Surfactants

Suitable nonionic surfactants are generally disclosed in U.S. Pat. No. 3,929,678, Laughlin et al, issued Dec. 30, 1975, at column 13, line 14 through column 16, line 6, incorporated herein by reference. Classes of useful nonionic surfactants include:

1. The polyethylene oxide condensates of alkyl phenols. These compounds include the condensation products of alkyl phenols having an alkyl group containing from about 6 to about 12 carbon atoms in either a straight chain or branched chain configuration with ethylene oxide, the ethylene oxide being present in an amount equal to from about 5 to about 25 moles of ethylene oxide per mole of alkyl phenol. Examples of compounds of this type include nonyl phenol condensed with about 9.5 moles of ethylene oxide per mole of nonyl phenol; dodecyl phenol condensed with about 12 moles of ethylene oxide per mole of phenol; dinonyl phenol condensed with about 15 moles of ethylene oxide per mole of phenol; and diisooctyl phenol condensed with about 15 moles of ethylene oxide per mole of phenol. Commercially available nonionic surfactants of this type include Igepal CO-630, marketed by the GAF Corporation; and Triton X-45, X-114, X-100, and X-102, all marketed by the Rohm & Haas Company.

2. The condensation products of aliphatic alcohols with from about 1 to about 25 moles of ethylene oxide. The alkyl chain of the aliphatic alcohol can either be straight or branched, primary or secondary, and generally contains from about 8 to about 22 carbon atoms. Particularly preferred are the condensation products of alcohols having an alkyl group containing from about 10 to about 20 carbon atoms with from about 4 to about 10 moles of ethylene oxide per mole of alcohol. Examples of such ethoxylated alcohols include the condensation product of myristyl alcohol with about 10 moles of ethylene oxide per mole of alcohol; and the condensation product of coconut alcohol (a mixture of fatty alcohols with alkyl chains varying in length from 10 to 14 carbon atoms) with about 9 moles of ethylene oxide. Examples of commercially available nonionic surfactants of this type include Tergitol 15-S-9 (the condensation product of $C_{11}$–CHd 15 linear alcohol with 9 moles ethylene oxide), marketed by Union Carbide Corporation; Neodol 45-9 (the condensation product of $C_{14}$–$C_{15}$ linear alcohol with 9 moles of ethylene oxide), Neodol 23-6.5 (the condensation product of $C_{12}$–$C_{13}$ linear alcohol with 6.5 moles of ethylene oxide), Neodol 45-7 (the condensation product of $C_{14}$–$C_{15}$ linear alcohol with 7 moles of ethylene oxide), Neodol 45-4 (the condensation product of $C_{14}$–$C_{15}$ linear alcohol with 4 moles of ethylene oxide), marketed by Shell Chemical Company, and Kyro EOB (the condensation product of $C_{13}$–$C_{15}$ linear alcohol with 9 moles ethylene oxide), marketed by The Proctor & Gamble Company.

3. The condensation products of ethylene oxide with a hydrophobic base formed by the condensation of propylene oxide with propylene glycol. The hydrophobic portion of these compounds has a molecular weight of from about 1500 to about 1800 and exhibits water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide. Examples of compounds of this type include certain of the commercially available Pluronic surfactants, marketed by Wyandotte Chemical Corporation.

4. The condensation products of ethylene oxide with the product resulting from the reaction of propylene oxide and ethylenediamine. The hydrophobic moiety of these products consists of the reaction product of ethylenediamine and excess propylene oxide, and generally has a molecular weight of from about 2500 to about 3000. This hydrophobic moiety is condensed with ethylene oxide to the extent that the condensation product contains from about 40% to about 80% by weight of polyoxyethylene and has a molecular weight of from about 5,000 to about 11,000. Examples of this type of nonionic surfactant include certain of the commercially available Tetronic compounds, marketed by Wyandotte Chemical Corporation.

5. Semi-polar nonionic surfactants, which include water-soluble amine oxides containing one alkyl moiety of from about 10 to about 18 carbon atoms and 2 moieties selected from the group consisting of alkyl groups and hydroxyalkyl groups containing from about 1 to about 3 carbon atoms; water-soluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety of from about 10 to 18 carbon atoms and a moiety selected from the group consisting of alkyl and hydroxyalkyl moieties of from about 1 to 3 carbon atoms.

Preferred semi-polar nonionic detergent surfactants are the amine oxide surfactants having the formula

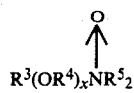

wherein $R^3$ is an alkyl, hydroxyalkyl, or alkyl phenyl group or mixtures thereof containing from about 8 to about 22 carbon atoms; $R^4$ is an alkylene or hydroxyalkylene group containing from about 2 to about 3 carbon atoms or mixtures thereof; x is from 0 to about 3; and each $R^5$ is an alkyl or hydroxyalkyl group containing from about 1 to about 3 carbon atoms or a polyethylene oxide group containing from about 1 to about 3 ethylene oxide groups. The $R^5$ groups can be attached to each other, e.g., through an oxygen or nitrogen atom, to form a ring structure.

Preferred amine oxide surfactants are $C_{10}$-$C_{18}$ alkyl dimethyl amine oxides and $C_8$-$C_{12}$ alkoxy ethyl dihydroxy ethyl amine oxides.

6. Alkylpolysaccharides disclosed in U.S. Pat. No. 4,565,647, Llenado, issued Jan. 21, 1986, having a hydrophobic group containing from about 6 to about 30 carbon atoms, preferably from about 10 to about 16 carbon atoms and a polysaccharide, e.g., a polyglycoside, hydrophilic group containing from about 1½ to about 10, preferably from about 1½ to about 3, most preferably from about 1.6 to about 2.7 saccharide units. Any reducing saccharide containing 5 or 6 carbon atoms can be used, e.g., glucose, galactose and galactosyl moieties can be substituted for the glucosyl moieties. (Optionally the hydrophobic group is attached at the 2-, 3-, 4-, etc. positions thus giving a glucose or galactose as opposed to a glucoside or galactoside). The intersaccharide bonds can be, e.g., between the 1-position of the additional saccharide units and the 2-, 3-, 4-, and/or 6-positions on the preceding saccharide units.

Optionally, and less desirably, there can be a polyalkyleneoxide chain joining the hydrophobic moiety and the polysaccharide moiety. The preferred alkyleneoxide is ethylene oxide. Typical hydrophobic groups include alkyl groups, either saturated or unsaturated, branched or unbranched containing from about 8 to about 18, preferably from about 10 to about 16, carbon atoms. Preferably, the alkyl group is a straight chain saturated alkyl group. The alkyl group can contain up to 3 hydroxy groups and/or the polyalkyleneoxide chain can contain up to about 10, preferably less than 5, alkyleneoxide moieties. Suitable alkyl polysaccharides are octyl, nonyldecyl, undecyl, dodecyl, tridecyl, tetradecyl, pentadecyl, hexadecyl, heptadecyl, and octadecyl, di-, tri-, tetra-, penta-, and hexaglucosides, galactosides, lactosides, glucoses, fructosides, fructoses and/or galactoses. Suitable mixtures include coconut alkyl, di-, tri-, tetra-, and pentaglucosides and tallow alkyl tetra-, penta-, and hexaglucosides.

The preferred alkylpolyglycosides have the formula $$R^2O(C_nH_{2n}O)_t(glycosyl)_x$$

wherein $R^2$ is selected from the group consisting of alkyl, alkylphenyl, hydroxyalkyl, hydroxyalkyphenyl, and mixtures thereof in which the alkyl groups contain from about 10 to about 18, preferably from about 12 to about 14, carbon atoms; n is 2 or 3, preferably 2; t is from 0 to about 10, preferably 0; and x is from about 1½ to about 10, preferably from about 1½ to about 3, most preferably from about 1.6 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl unit's 2-, 3-, 4- and/or 6-position, preferably predominantly the 2-position.

7. Fatty acid amide surfactants having the formula:

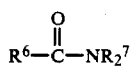

wherein $R^6$ is an alkyl group containing from about 7 to about 21 (preferably from about 9 to about 17) carbon atoms and each $R^7$ is selected from the group consisting of hydrogen, $C_1$-$C_4$ alkyl, $C_1$-$C_4$ hydroxyalkyl, and $-(C_2H_4O)_xH$ where x varies from about 1 to about 3.

Preferred amides are $C_8$-$C_{20}$ ammonia amides, monoethanolamides, diethanolamides, and isopropanolamides.

B. Anionic Surfactants

Anionic surfactants suitable for use in the present invention are generally disclosed in U.S. Pat. No. 3,929,678, Laughlin et al., issued Dec. 30, 1975, at column 23, line 58 through column 29, line 23, incorporated herein by reference. Classes of useful anionic surfactants include:

1. Ordinary alkali metal soaps, such as the sodium, potassium, ammonium and alkylolammonium salts of higher fatty acids containing from about 8 to about 24 carbon atoms, preferably from about 10 to about 20 carbon atoms. Preferred alkali metal soaps are sodium laurate, sodium stearate, sodium oleate and potassium palmitate.

2. Water-soluble salts, preferably the alkali metal, ammonium and alkylolammonium salts, of organic sulfuric reaction products having in their molecular structure an alkyl group containing from about 10 to about 20 carbon atoms and a sulfonic acid or sulfuric acid ester group. (Included in the term "alkyl" is the alkyl portion of acyl groups.)

Examples of this group of anionic surfactants are the sodium and potassium alkyl sulfates, especially those obtained by sulfating the higher alcohols ($C_8$-$C_{18}$ carbon atoms), such as those produced by reducing the glycerides of tallow or coconut oil; and the sodium and potassium alkylbenzene sulfonates in which the alkyl group contains from about 9 to about 15 carbon atoms, in straight chain or branched chain configuration, e.g., those of the type described in U.S. Pat. No. 2,220,099, Guenther et al., issued Nov. 5, 1940, and U.S. Pat. No. 2,477,38, Lewis, issued Dec. 26, 1946. Especially useful are linear straight chain alkylbenzene sulfonates in which the average number of carbon atoms in the alkyl group is from about 11 to about 13, abbreviated as $C_{11}$-$C_{13}$LAS.

Another group of preferred anionic surfactants of this type are the alkyl polyethoxylate sulfates, particularly those in which the alkyl group contains from about 10 to about 22, preferably from about 12 to about 18 carbon atoms, and wherein the polyethoxylate chain contains from about 1 to about 15 ethoxylate moieties, preferably from about 1 to about 3 ethoxylate moieties. These anionic detergent surfactants are particularly desirable for formulating heavy-duty liquid laundry detergent compositions.

Other anionic surfactants of this type include sodium alkyl glyceryl ether sulfonates, especially those ethers of higher alcohols derived from tallow and coconut oils; sodium coconut oil fatty acid monoglyceride sulfonates and sulfates; sodium or potassium salts of alkyl phenol ethylene oxide ether sulfates containing from about 1 to about 10 units of ethylene oxide per molecule and wherein the alkyl groups contain from about 8 to about 12 carbon atoms; and sodium or potassium salts of alkyl ethylene oxide ether sulfates containing about 1 to about 10 units of ethylene oxide per molecule and wherein the alkyl group contains from about 10 to about 20 carbon atoms.

Also included are water-soluble salts of esters of alpha-sulfonated fatty acids containing from about 6 to about 20 carbon atoms in the fatty acid group and from about 1 to about 10 carbon atoms in the ester group; water-soluble salts of 2-acyloxyalkane-1-sulfonic acids containing from about 2 to about 9 carbon atoms in the acyl group and from about 9 to about 23 carbon atoms in the alkane moiety; alkyl ether sulfates containing from about 10 to about 20 carbon atoms in the alkyl group and from about 1 to about 30 moles of ethylene oxide; water-soluble salts of olefin sulfonates containing from about 12 to about 24 carbon atoms; and beta-alkyloxy alkane sulfonates containing from about 1 to about 3 carbon atoms in the alkyl group and from about 8 to about 20 carbon atoms in the alkane moiety.

Particularly preferred surfactants for use herein include alkyl benzene sulfonates, alkyl sulfates, alkyl polyethoxy sulfates and mixtures thereof. Mixtures of these anionic surfactants with a nonionic surfactant selected from the group consisting of $C_{10}$-$C_{20}$ alcohols ethoxylated with an average of from about 4 to about 10 moles of ethylene oxide per mole of alcohol are particularly preferred.

3. Anionic phosphate surfactants.

4. N-alkyl substituted succinamates.

C. Ampholytic Surfactants

Ampholytic surfactants can be broadly described as aliphatic derivatives of secondary or tertiary amines, or aliphatic derivatives of heterocyclic secondary and tertiary amines in which the aliphatic radical can be straight or branched chain and wherein one of the aliphatic substituents contains from about 8 to about 18 carbon atoms and at least one of the aliphatic substituents contains an anionic water-solubilizing group, e.g., carboxy, sulfonate, sulfate. See U.S. Pat. No. 3,929,678, Laughlin et al., issued Dec. 30, 1975, column 19, line 38 through column 22, line 48, incorporated herein by reference, for examples of ampholytic surfactants useful herein.

D. Zwitterionic Surfactants

Zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678, Laughlin et al., issued Dec. 30, 1975, column 19, line 38 through column 22, line 48, incorporated herein by reference, for examples of zwitterionic surfactants useful herein.

E. Cationic Surfactants

Cationic surfactants can also be included in detergent compositions of the present invention. Cationic surfactants comprise a wide variety of compounds generally containing at least one quaternary nitrogen and generally associated with an anionic radical. Pentavalent nitrogen ring compounds are also considered quaternary nitrogen compounds. Suitable anions are halides, methyl sulfate and hydroxide. Tertiary amines can have characteristics similar to cationic surfactants when present in laundry compositions at pH values less than about 8.5.

Suitable cationic surfactants include the quaternary ammonium surfactants having the formula:

$$[R^2(OR^3)_y][R^4(OR^3)_y]_2R^5N^+X^-$$

wherein $R^2$ is an alkyl or alkyl benzyl group having from about 8 to about 18 carbon atoms in the alkyl chain; each $R^3$ is independently selected from the group consisting of —$CH_2CH_2$—, —$CH_2CH(CH_3)$—, —$CH_2CH(CH_2OH)$—, and —$CH_2CH_2CH_2$—; each $R^4$ is independently selected from the group consisting of $C_1$-$C_4$ alkyl, $C_1$-$C_4$ hydroxyalkyl, benzyl, ring structures formed by joining the two $R^4$ groups, —$CH_2$-$CHOHCHOHCOR^6CHOHCH_2OH$ wherein $R^6$ is any hexose or hexose polymer having a molecular weight less than about 1000, and hydrogen when y is not 0; $R^5$ is the same as $R^4$ or is an alkyl chain wherein the total number of carbon atoms of $R^2$ plus $R^5$ is not more than about 18; each y is from 0 to about 10 and the sum of the y values is from 0 to about 15; and X is any compatible anion.

Preferred examples of the above compounds are the alkyl quaternary ammonium surfactants, especially the mono-long chain alkyl surfactants described in the above formula when $R^5$ is selected from the same groups as $R^4$. The most preferred quaternary ammonium surfactants are the chloride, bromide and methylsulfate $C_8$-$C_{16}$ alkyl trimethylammonium salts, $C_8$-$C_{16}$ alkyl di(hydroxyethyl)methylammonium salts, the $C_8$-$C_{16}$ alkyl hydroxyethyldimethylammonium salts, and $C_8$-$C_{16}$ alkyloxypropyltrimethylammonium salts. Of the above, decyl trimethylammonium methylsulfate, lauryl trimethylammonium chloride, myristyl trimethylammonium bromide and coconut trimethylammonium chloride and methylsulfate are particularly preferred.

A more complete disclosure of cationic surfactants useful herein can be found in U.S. Pat. No. 4,228,044, Cambre, issued Oct. 14, 1980, incorporated herein by reference.

Detergent Builders

Detergent compositions of the present invention contain inorganic and/or organic detergent builders to assist in mineral hardness control. These builders comprise from about 5% to about 80% by weight of the compositions. Built liquid formulations preferably comprise from about 10% to about 30% by weight of detergent builder, while built granular formulations preferably comprise from about 10% to about 50% by weight of detergent builder.

Suitable detergent builders include crystalline aluminosilicate ion exchange materials having the formula:

$$Na_z[(AlO_2)_z(SiO_2)_y] \cdot xH_2O$$

wherein z and y are at least about 6, the mole ratio of z to y is from about 1.0 to about 0.5; and x is from about 10 to about 264.

Amorphous hydrated aluminosilicate materials useful herein have the empirical formula $$M_x(zAlO_2 \cdot ySiO_2)$$

wherein M is sodium, potassium, ammonium or substituted ammonium, z is from about 0.5 to about 2, and y is 1; this material having a magnesium ion exchange capacity of at least about 50 milligram equivalents of $CaCO_3$ hardness per gram of anhydrous aluminosilicate.

The aluminosilicate ion exchange builder materials are in hydrated form and contain from about 10% to about 28% of water by weight if crystalline, and potentially even higher amounts of water if amorphous. Highly preferred crystalline aluminosilicate ion exchange materials contain from about 18% to about 22% water in their crystal matrix. The preferred crystalline aluminosilicate ion exchange materials are further characterized by a particle size diameter of from about 0.1 micron to about 10 microns. Amorphous materials are often smaller, e.g., down to less than about 0.01 micron. More preferred ion exchange materials have a particle size diameter of from about 0.2 micron to about 4 microns. The term "particle size diameter" represents the average particle size diameter of a given ion exchange material as determined by conventional analytical techniques such as, for example, microscopic determination utilizing a scanning electron microscope. The crystalline aluminosilicate ion exchange materials are usually further characterized by their calcium ion exchange capacity, which is at least about 200 mg. equivalent of $CaCO_3$ water hardness/g. of aluminosilicate, calculated on an anhydrous basis, and which generally is in the range of from about 300 mg. eq./g. to about 352 mg. eq./g. The aluminosilicate ion exchange materials are still further characterized by their calcium ion exchange rate which is at least about 2 grains $Ca^{++}$/gallon/minute/gram/gallon of aluminosilicate (anhydrous basis), and generally lies within the range of from about 2 grains/gallon/minute/gram/gallon to about 6 grains/gallon/minute/gram/gallon, based on calcium ion hardness. Optimum aluminosilicates for builder purposes exhibit a calcium ion exchange rate of at least about 4 grains/gallon/minute/gram/gallon.

The amorphous aluminosilicate ion exchange materials usually have a $Mg^{++}$ exchange capacity of at least about 50 mg. eq. $CaCO_3$/g. (12 mg. $Mg^{++}$/g.) and a $Mg^{++}$ exchange rate of at least about 1 grain/gallon/minute/gram/gallon. Amorphous materials do not exhibit an observable diffraction pattern when examined by Cu $K\alpha$ radiation (wavelength 1.54 Angstrom Units).

Aluminosilicate ion exchange materials useful herein are commercially available. These aluminosilicates can be crystalline or amorphous in structure and can be naturally-occurring aluminosilicates or synthetically derived. A method for producing aluminosilicate ion exchange materials is disclosed in U.S. Pat. No. 3,985,669, Krummel et al, issued Oct. 12, 1976, incorporated herein by reference. Preferred synthetic crystalline aluminosilicate ion exchange materials useful herein are available under the designations Zeolite A, Zeolite P (B), and Zeolite X. In an especially preferred embodiment, the crystalline aluminosilicate ion exchange material has the formula $$Na_{12}[(AlO_2)_{12}(SiO_2)_{12}] \cdot xH_2O$$

wherein x is from about 20 to about 30, especially about 27.

Other detergency builders useful in the present invention include the alkali metal silicates, alkali metal carbonates, phosphates, polyphosphates, phosphonates, polyphosphonic acids, $C_{10-18}$ alkyl monocarboxylic acids, polycarboxylic acids, alkali metal ammonium or substituted ammonium salts thereof and mixtures thereof. Preferred are the alkali metal, especially sodium, salts of the above.

Specific examples of inorganic phosphate builders are sodium or potassium tripolyphosphate, sodium or potassium pyrophosphate, sodium or potassium polymeric metaphosphate having a degree of polymerization of from about 6 to about 21, and sodium or potassium orthophosphate. Examples of polyphosphonate builders are the sodium and potassium salts of ethylene-1,1-diphosphonic acid, the sodium and potassium salts of ethane-1-hydroxy-1,1-diphosphonic acid, and the sodium and potassium salts of ethane-1,1,2-triphosphonic acid. Other suitable phosphorus builder compounds are disclosed in U.S. Pat. No. 3,159,581, Diehl, issued Dec. 1, 1964; U.S. Pat. No. 3,213,030, Diehl, issued Oct. 19, 1965; U.S. Pat. No. 3,400,148, Quimby, issued Sept. 3, 1968; U.S. Pat. No. 3,400,176, Quimby, issued Sept. 3, 1968; U.S. Pat. No. 3,422,021, Roy, issued Jan. 14, 1969; and U.S. Pat. No. 3,422,137, Quimby, issued Sept. 3, 1968; all herein incorporated by reference. However, while suitable for use in compositions of the invention, one of the advantages of the present invention is that effective detergent compositions can be formulated using minimum levels or in the complete absence of phosphonates and phosphates.

Examples of nonphosphorus, inorganic builders are sodium or potassium carbonate, sodium or potassium bicarbonate, sodium or potassium sesquicarbonate, sodium or potassium tetraborate decahydrate, and sodium or potassium silicate having a mole ratio of $SiO_2$ to alkali metal oxide of from about 0.5 to about 4.0, preferably from about 1.0 to about 2.4.

Useful water-soluble, nonphosphorus organic builders include the various alkali metal, ammonium and substituted ammonium polyacetates, carboxylates, polycarboxylates and polyhydroxysulfonates. Examples of polyacetate and polycarboxylate builders are the sodium, potassium, lithium, ammonium and substituted ammonium salts of ethylenediamine tetraacetic acid, nitrilotriacetic acid, oxydisuccinic acid, mellitic acid, benzene polycarboxylic acids, and citric acid.

Highly preferred polycarboxylate builders are disclosed in U.S. Pat. No. 3,308,067, Diehl, issued Mar. 7, 1967 incorporated herein by reference. Such materials include the water-soluble salts of homo- and copolymers of aliphatic carboxylic acids, such as maleic acid, itaconic acid, mesaconic acid, fumaric acid, aconitic acid, citraconic acid and methylenemalonic acid.

Other builders include the carboxylated carbohydrates disclosed in U.S. Pat. No. 3,723,322, Diehl, issued Mar. 28, 1973, incorporated herein by reference.

A class of useful phosphorus-free detergent builder materials have been found to be ether polycarboxylates.

A number of ether polycarboxylates have been disclosed for use as detergent builders. Examples of useful ether polycarboxylates include oxydisuccinates, as disclosed in Berg, U.S. Pat. No. 3,128,287, issued Apr. 7, 1964, and Lamberti et al, U.S. Pat. No. 3,635,830, issued Jan. 18, 1972, both of which are incorporated herein by reference.

A specific type of ether polycarboxylates useful as builders in the present invention are those having the general formula:

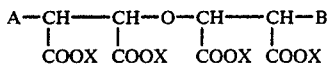

wherein A is H or OH; B is H or

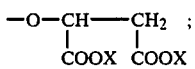

and X is H or a salt-forming cation. For example, if in the above general formula A and B are both H, then the compound is oxydissuccinic acid and its water-soluble salts. If A is OH and B is H, then the compound is tartrate monosuccinic acid (TMS) and its water-soluble salts. If A is H and B is

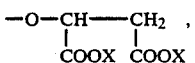

then the compound is tartrate disuccinic acid (TDS) and its water-soluble salts. Mixtures of these builders are especially preferred for use herein. Particularly preferred are mixtures of TMS and TDS in a weight ratio of TMS to TDS of from about 97:3 to about 20:80. A more complete disclosure of these ether polycarboxylates is contained in U.S. Ser. No. 823,909, filed Jan. 30, 1986, Bush et al., incorporated herein by reference.

Suitable ether polycarboxylates also include cyclic compounds, particularly alicyclic compounds, such as those described in U.S. Pat. Nos. 3,923,679; 3,835,163; 4,158,635; 4,120,874 and 4,102,903, all of which are incorporated herein by reference.

Other useful detergency builders include the ether hydroxypolycarboxylates represented by the structure:

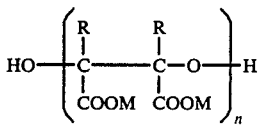

wherein M is hydrogen or a cation wherein the resultant salt is water soluble, preferably an alkali metal, ammonium or substituted ammonium cation, n is from about 2 to about 15 (preferably n is from about 2 to about 10, more preferably n averages from about 2 to about 4) and each R is the same or different and selected from hydrogen, $C_{1-4}$ alkyl or $C_{1-4}$ substituted alkyl (preferably R is hydrogen). A more complete disclosure of these ether polycarboxylates is contained in U.S. Ser. No. 754,560, filed July 11, 1985, Bush et al, incorporated herein by reference.

Also suitable in the detergent compositions of the present invention are the 3,3-dicarboxy-4-oxa-1,6-hexanedioates and the related compounds disclosed in U.S. Pat. No. 4,566,984, Bush, issued Jan. 28, 1986, incorporated herein by reference. Other useful builders include the $C_5$-$C_{20}$ alkyl succinic acids and salts thereof. A particularly preferred compound of this type is dodecenylsuccinic acid.

Useful builders also include sodium and potassium carboxymethyloxymalonate, carboxymethyloxysuccinate, cis-cyclohexanehexacarboxylate, cis-cyclopentanetetracarboxylate phloroglucinol trisulfonate, water-soluble polyacrylates (having molecular weights of from about 2,000 to about 200,000, for example), and the copolymers of maleic anhydride with vinyl methyl ether or ethylene.

Other suitable polycarboxylates are the polyacetal carboxylates disclosed in U.S. Pat. No. 4,144,226, Crutchfield et al, issued Mar. 13, 1979, incorporated herein by reference. These polyacetal carboxylates can be prepared by bringing together, under polymerization conditions, an ester of glyoxylic acid and a polymerization initiator. The resulting polyacetal carboxylate ester is then attached to chemically stable end groups to stabilize the polyacetal carboxylate against rapid depolymerization in alkaline solution, converted to the corresponding salt, and added to a surfactant.

Especially useful detergency builders include the $C_{10}$-$C_{18}$ alkyl monocarboxylic (fatty) acids and salts thereof. These fatty acids can be derived from animal and vegetable fats and oils, such as tallow, coconut oil and palm oil. Suitable saturated fatty acids can also be synthetically prepared (e.g., via the oxidation of petroleum or by hydrogenation of carbon monoxide via the Fisher-Tropsch process). Particularly preferred $C_{10}$-$C_{18}$ alkyl monocarboxylic acids are saturated coconut fatty acids, palm kernel fatty acids, and mixtures thereof.

Other useful detergency builder materials are the "seeded builder" compositions disclosed in Belgian Pat. No. 798,856, published Oct. 29, 1973, incorporated herein by reference. Specific examples of such seeded builder mixtures are 3:1 wt. mixtures of sodium carbonate and calcium carbonate having 5 micron particle diameter; 2.7:1 wt. mixtures of sodium sesquicarbonate and calcium carbonate having a particle diameter of 0.5 microns; 20:1 wt. mixtures of sodium sesquicarbonate and calcium hydroxide having a particle diameter of 0.01 micron; and a 3:3:1 wt. mixture of sodium carbonate, sodium aluminate and calcium oxide having a particle diameter of 5 microns.

Optional Detergent Ingredients

Other optional ingredients which can be included in detergent compositions of the present invention, in their conventional art-established levels for use (generally from 0 to about 20% of the detergent composition), include solvents, hydrotropes, solubilizing agents, processing aids, corrosion inhibitors, dyes, fillers, optical brighteners, germicides, pH-adjusting agents (monoethanolamine, sodium carbonate, sodium hydroxide, etc.), enzymes, enzyme-stabilizng agents, perfumes, fabric softening components, static control agents, bleaching agents, bleach activators, bleach stabilizers and the like.

General Detergent Formulations

Useful laundering and fabric care compositions of the invention may be formulated as bars, powders, granules, tablets, liquids or flowable gels or on carrier substrates or in pouches wherein the said anionic oligomeric esters are present in releasable form.

A preferred form of laundering and fabric care composition of the invention is a liquid detergent composition containing the aforesaid esters and optionally also comprising fabric care agents which are fabric softeners and/or antistatic agents. A highly preferred form of laundering and fabric care composition of the invention is an isotropic liquid detergent composition.

Granular formulations embodying the detergent compositions of the present invention can be formed by conventional techniques, i.e., by slurrying the individual components in water and then atomizing and spray-drying the resultant mixture, or by pan or drum granulation of the ingredients. Granular formulations preferably comprise from about 10 to about 30% detergent surfactant, usually anionic, and most preferably about 15 to about 25% surfactant.

Liquid formulations embodying the detergent compositions can be built or unbuilt. If unbuilt, these compositions contain approximately 15 to 50% (preferably about 20 to 35%) total surfactant; from 0 to 5% (preferably from 0 to 2%) of an organic base, such as a mono-, di-, or tri-alkanol amine; a neutralization system, such as an alkali metal hydroxide; a lower primary alcohol, such as ethanol or isopropanol; and approximately 20 to 80% water.

Built liquid detergent compositions can be in the form of single phase liquids provided that the builder is solubilized in the mixture at its level of use. Such liquids conventionally contain about 10 to 40% (preferably about 15 to 25%) total surfactant, about 1 to 25% (preferably about 3 to 20%) builder which can be organic or inorganic, up to about 10% of a hydrotrope system, and about 20 to 80% water. Built liquid detergents incorporating components that form heterogeneous mixtures (or levels of builder that cannot be completely dissolved) can also comprise detergent compositions of the present invention. Such liquids conventionally employ viscosity modifiers to produce systems having plastic shear characteristics to maintain stable dispersions and to prevent phase separation or solid settlement.

To ensure that hydrolysis of the anionic oligomeric esters does not occur during formulation or storage of the consumer laundering and fabric care compositions of the invention, the esters sould generally not be exposed to extremes of pH. Consumer products are generally formulated for mildness, for fabric care and for maximum stability of ingredients such as enzymes, in a pH range between about 4 and about 10.5, more preferably between about 5 and about 8.5 (measured in 1.0 wt % aqueous solution).

Specific Examples of Consumer Laundering and Fabric Care Compositions According to the Present Invention

EXAMPLE V

A soil-releasing detergent composition is made by mixing the ingredients described as follows:

| Ingredients | Wt. % |
| --- | --- |
| Anionic oligomeric esters of Example I | 5 |
| $C_{13}$ linear alkylbenzenesulfonic acid, sodium salt | 60 |
| $C_{12}$–$C_{13}$ alcohol polyethoxylate (6.5) | 35 |

The composition of Example V is added to an aqueous laundry bath at a concentration of 1000 ppm to provide fabric cleaning and soil release performance.

EXAMPLE VI

A soil-releasing detergent composition is made by mixing ingredients as follows:

| Ingredients | Wt. % |
| --- | --- |
| Anionic oligomeric esters of Example II | 3 |
| $C_{13}$ linear alkylbenzenesulfonic acid, sodium salt | 50 |
| $C_{12}$–$C_{13}$ alcohol polyethoxylate (6.5) | 40 |

The composition of Example VI is added to an aqueous laundry bath at a concentration of 1250 ppm to provide fabric cleaning and soil release performance.

EXAMPLE VII

A soil-releasing detergent composition is made by mixing ingredients as follows:

| Ingredients | Wt. % |
| --- | --- |
| Anionic oligomeric esters of Example III | 3 |
| $C_{13}$ linear alkylbenzenesulfonic acid, sodium salt | 50 |
| $C_{12}$–$C_{13}$ alcohol polyethoxylate (6.5) | 47 |

The composition of Example VII is added to an aqueous laundry bath at a concentration of 1200 ppm to provide fabric cleaning and soil release performance.

EXAMPLE VIII

A composition of the type shown below is prepared as premeasured, 50-gram sachets, using water-permeable, nonwoven cloth as the sachet material. The sachets are simply placed in an aqueous fabric treatment bath to provide soil release performance benefits when said aqueous bath is used for soaking fabrics.

| Ingredients | Wt. % |
| --- | --- |
| Anionic oligomeric esters of Example IV* | 10 |
| Sodium sulfate | 90 |

*Sprayed onto sodium sulfate and air-dried.

EXAMPLE IX

A soil-releasing granular detergent composition is as follows:

| Component | Wt. % |
| --- | --- |
| Anionic oligomeric esters of Example I* | 2.0 |
| Sodium $C_{14}$–$C_{15}$ alkylethoxysulfate | 10.7 |
| $C_{13}$ linear alkyl benzene sulfonic acid | 4.3 |
| $C_{12}$–$C_{14}$ alkylpolyethoxylate (6) | 0.5 |
| $C_{12}$ alkyltrimethyl ammonium chloride | 0.5 |
| Sodium toluene sulfonate | 1.0 |
| Sodium tripolyphosphate | 32.9 |
| Sodium carbonate | 20.3 |
| Sodium silicate | 5.8 |
| Minors and water | Balance to 100 |

*Enrobed in PEG having an average M.W. 8,000 to provide protection from locally high concentrations of alkali.

Except for the enrobed oligomeric ester particles, the components are added together with continuous mixing to form an aqueous slurry which is then spray dried to form granules. The enrobed oligomeric ester particles are then mixed with the granules to form the composition. An aqueous laundry bath using a concentration of 1500 ppm of the detergent composition of Example IX is used at 40° C. for washing fabrics and providing soil release benefits.

EXAMPLE X

A soil-releasing, fabric-softening granular detergent composition is as follows:

| Ingredient | Wt. % |
|---|---|
| Anionic oligomeric esters of Example III* | 2.0 |
| $C_{12}$-$C_{13}$ alcohol polyethoxylate (6.5) | 20.0 |
| Magnesium sulfate | 1.0 |
| Zeolite 4A, hydrate (1–10 micron size) | 26.0 |
| Sodium carbonate | 18.3 |
| Sodium bicarbonate | 15.7 |
| Fabric softening clay+ | 3.0 |
| Fluorescent brightener | 1.7 |
| Minors (including brighteners, enzymes) | Balance to 100 |

*Enrobed in PEG having an average M.W. 8,000 to provide protection from locally high concentrations of alkali.
+Preferred fabric softening clays are essentially pure, white, impalpable smectite/montmorillonites having cation exchange capacities about 100 meq/100 g obtainable from Southern Clay Co. (formerly Georgia Kaolin Co.). An aqueous laundry bath using a concentration of 1500 ppm of the detergent composition of Example X is used at 40° C. for washing fabrics and providing soil-release and fabric-softening benefits.

EXAMPLES XI–XVI

Liquid detergent compositions are formulated as follows:

| | Wt. % | | | | | |
|---|---|---|---|---|---|---|
| Component | XI | XII | XIII | XIV | XV | XVI |
| Anionic oligomeric esters of Example IV* | 1 | 2 | 0.3 | 0.5 | 0.5 | 3 |
| $C_{12}$ linear alkylbenzene sulfonate, acid form | 8 | 25 | — | — | 8 | 30 |
| Sodium $C_{12}$ alkylethoxy (2) sulfate | 12 | — | 23 | 18 | 12 | — |
| $C_{12}$-$C_{13}$ alcohol polyethoxylate (6.5) | 5 | 6 | — | 5 | 2 | — |
| $C_{12}$-$C_{14}$ trimethylammonium chloride | 0.5 | — | — | — | 0.5 | — |
| n-dodecyldimethylamine N—oxide | — | 0.5 | — | — | — | — |
| Sodium citrate | 4 | 3 | 5 | 5 | 5 | 3 |
| Lauric/myristic acids, 3:1 ratio | 11 | 10 | 3 | 3 | 3 | 8 |
| Tartrate monosuccinate/tartrate disuccinate, sodium salts, 80:20 | — | — | 5 | 5 | 5 | — |
| Ethanol | 9 | — | — | — | — | — |
| Monoethanolamine | 2 | 7 | 1.5 | 2 | 1.5 | 3 |
| 1,2-propylene glycol | 4 | 11 | 4 | 4 | 4 | 15 |
| Sodium cumene sulfonate | — | — | 3 | 3 | 3 | — |
| Minors and water, including enzymes, optical brighteners and perfume | Balance to 100 | | | | | |

* Esters having higher ethoxylation, such as those of Example IV, are preferred herein when compared with lower ethoxylates, such as those of Example I.

The components are added together with continuous mixing to form the compositions, which may be used at concentrations ranging from 1200 to 2500 ppm in aqueous laundry baths at 20°–40° C. to wash and provide soil release benefits to fabrics, particularly those made of polyesters.

EXAMPLE XVII

A fabric softener base-composition is prepared from the following ingredients:

| Ingredient | Wt. % |
|---|---|
| Ditallow dimethyl ammonium chloride | 4.3 |
| 1-Methyl-1-tallowamidoethyl-2-tallowimidazolinium methylsulfate (Varisoft 475)+ | 1.0 |
| Ethanol | 0.7 |
| Isopropanol | 0.1 |
| Perfume | 0.42 |
| Dye | 0.1 |
| Minors* | up to 0.1 |
| Water | Balance |

*preservative, NaCl, NaOH, $H_2SO_4$, antioxidant solution. To this base composition is added 1% by weight of the anionic oligomeric esters of Examples I, II, III or IV, providing combined fabric softening and soil-release treatment compositions for use in rinse-added mode.
+Sherex Co.

EXAMPLE XVIII

Fabric-conditioning sheets for use in a tumble-dryer are formulated as follows:

| | Wt. % | |
|---|---|---|
| Ingredient | A | B |
| Anionic Oligomeric Esters of Example II | 37.5 | 67.0 |
| Fabric Softening Agents | | |
| Ditallowdimethylammonium methylsulfate | 11.25 | — |
| Ditallow methylamine | 11.25 | — |
| Sorbitan monostearate | 22.5 | 33.0 |
| $C_{16}$-$C_{18}$ Fatty Alcohol | 12.5 | — |
| Fabric softening clay$^a$ | 5.0 | — |

$^a$As in Example X.

Mixtures A and B are prepared and combined in 70:30 (wt%) proportion by heating together at 70° C. Nonwoven substrate, comprised of 70% 3-denier, 0.16–1.43 cm long rayon fibers with 30% polyvinyl acetate binder, is cut into 23 by 28 cm sheets. Each such sheet is treated as follows: slightly more than target coating weight, being about 2.5 grams of the A+B admixture per 23×28 cm sheet, is distributed on a heating plate and a 23×28 cm sheet of nonwoven cloth is placed over it. A small paint roller is used to impregnate the mixture into the interstices of the sheet. The impregnated sheet is removed from the hot plate and allowed to cool to room temperature whereby the mixture solidifies. Following solidification of the fabric conditioning component, the impregnated sheet is slit with a knife. (Conveniently, the 23×28 cm sheet is provided with 3 to 9 rectilinear slits extending along one dimension of the sheet, the slits being in substantially parallel relationship and extending to within about 2.5 cm from at least one edge of said dimension of the sheet). The width of an individual slit is about 0.5 cm.

Anionic oligomeric esters of the invention are applied, together with fabric softeners, to consumers' fabrics, by placing one or more of the impregnated sheets together with said fabrics in a tumble-dryer operating at 50°–80° C., to provide combined soil-release and fabric softening benefits thereto.

What is claimed is:

1. Oligomeric esters having at least one anionic substituent group, said esters having the formula

[Q—Z—O—R—O]$_x$Z—Q'  I or

Q''$\{$Z—O—R—O$\}_y$H  II or mixtures thereof; wherein Q, Q' and Q'' may be the same or different anionic substituents selected from the group consisting of MO$_3$S(CH$_2$CH$_2$O)$_n$—, MO$_3$S—(L)-$_q$(YO)$_m$(CH$_2$CH$_2$O)$_r$ and mixtures thereof, wherein M is H or a salt-forming cation, L is phenoethoxy, phenoxypropoxy or C$_1$-C$_6$ alkoxy, Y is —CH$_2$CH(CH$_3$)— or —CH(CH$_3$)CH$_2$—, n is an integer from 1 to 30, q is 1 or 0, m is an integer from 0 to 15 provided that m+q is at least 1 and r is an integer from 0 to 30; x and y may be the same or different and are each integers with x selected from 0 to 20 and y selected from 1 to 20; the R-substituents may be the same or different alkylene substituents selected from the group consisting of —CH$_2$CH$_2$—, —CH$_2$CH(X)— and —CH(X)CH$_2$— wherein X is methyl, ethyl, methoxymethyl, or C$_1$-C$_4$-alkylpoly(oxyalkylene)oxymethyl, or mixtures thereof; and the Z-substituents may be the same or different aryldicarbonyl substituents selected from the group consisting of

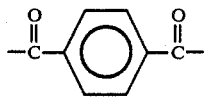

and mixtures thereof with aryl-1,3-dicarbonyl or substituted aryl-1,3-dicarbonyl or substituted aryl-1,4-dicarbonyl groups.

2. Oligomeric esters or mixtures thereof according to claim 1 wherein x and y are integers below 8, and the Z-substituents are

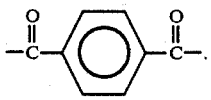

3. Oligomeric esters according to claim 1 wherein x is an integer from 3 to 7 and y is an integer from 4 to 8.

4. Mixtures of anionic oligomeric esters according to claim 1 wherein Z is

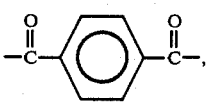

all R substituents are independently selected from —CH$_2$CH$_2$—, —CH$_2$CH(CH$_3$)— and —CH(CH$_3$)CH$_2$—, and Q, Q' and Q'' may be the same or different and are each selected from NaO$_3$S(CH$_2$CH$_2$O)$_n$ wherein n is an integer from 2 to 15.

5. Mixtures of anionic oligomeric esters according to claim 4 wherein the weight ratio of esters having formula I and esters having formula II is from about 30:1 to about 1:20.

6. Mixtures of anionic oligomeric esters according to claim 4 wherein the molar ratio of R substituents being —CH$_2$CH$_2$— substituents to R substituents being —CH$_2$CH(CH$_3$)— and —CH(CH$_3$)CH$_2$— substituents is from about 0:1 to about 0.9:0.1.

7. Mixtures of anionic oligomeric esters according to claim 4 wherein at least 2% by weight of the esters having formula I or II contain from 4

units to about 8

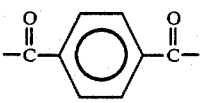

units.

8. Mixtures of anionic oligomeric esters according to claim 4 wherein the weight ratio of esters having formula I and esters having formula II is from about 30:1 to about 1:1 and wherein the molar ratio of R substituents being —CH$_2$CH$_2$— substituents to R substituents being —CH$_2$CH(CH$_3$)— and —CH(CH$_3$)CH$_2$— substituents is from about 0:1 to about 0.7:0.3 and wherein at least 2% by weight of the esters having formula I or II contain at least 4

units.

9. A laundering and fabric care composition comprising from about 0.1% to about 50% by weight of a soil release component comprising anionic oligomeric esters and mixtures of anionic oligomeric esters of claim 1.

10. A detergent composition comprising from about 1% to about 50% by weight of a detersive surfactant selected from the group consisting of anionic surfactants, cationic surfactants, nonionic surfactants, zwitterionic surfactants and mixtures thereof, and from about 0.1% to about 50% by weight of anionic oligomeric esters or mixtures of anionic oligomeric esters according to claim 1.

11. A detergent composition according to claim 10 wherein the detersive surfactant component comprises at least one anionic detersive surfactant.

12. A composition according to claim 10 which is formulated as a liquid laundry detergent.

13. A composition according to claim 9 which is formulated as a bar, powder, granule, tablet or flowable gel, or is releasably contained in pouch or sheet form or in or upon other carrier substrate.

14. A composition according to claim 10 which is formulated as a bar, powder, granule, tablet or flowable gel, or is releasably contained in pouch or sheet form or in or upon other carrier substrate.

15. A detergent composition comprising from about 1% to about 30% by weight of a detersive surfactant selected from the group consisting of anionic surfactants, cationic surfactants, nonionic surfactants, zwitterionic surfactants and mixtures thereof and from about 0.1% to about 4% by weight of anionic oligomeric esters or mixtures of anionic oligomeric esters according to claim 4.

16. A detergent composition comprising from about 1% to about 30% by weight of a detersive surfactant selected from the group consisting of anionic surfactants, cationic surfactants, nonionic surfactants, zwitterionic surfactants and mixtures thereof and from about 0.1% to about 4% by weight of anionic oligomeric esters or mixtures of anionic oligomeric esters according to claim 8.

17. A heavy-duty liquid detergent composition comprising, by weight:

(a) from about 10% to about 35% of an anionic surfactant on an acid basis;

(b) from 0% to about 15% of an ethoxylated nonionic surfactant of the formula $R^1(OC_2H_4)_jOH$, wherein $R^1$ is a $C_{10}$-$C_{16}$ alkyl group or a $C_8$-$C_{12}$ alkyl phenyl group, j averages from about 3 to about 9, and said nonionic surfactant has an HLB of from about 10 to about 13;

(c) from about 0% to about 15% of a cosurfactant selected from the group consisting of:

(i) quaternary ammonium surfactants having the formula:

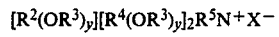

wherein $R^2$ is an alkyl or alkyl benzyl group having from about 6 to about 16 carbon atoms in the alkyl chain; each $R^3$ is selected from the group consisting of —CH$_2$CH$_2$—, —CH$_2$CH(CH$_3$)—, —CH(CH$_3$)CH$_2$—, —CH$_2$CH(CH$_2$OH)—, —CH$_2$CH$_2$CH$_2$—, and mixtures thereof; each $R^4$ is selected from the group consisting of $C_1$-$C_4$ alkyl, $C_1$-$C_4$ hydroxyalkyl, benzyl, and hydrogen when y is not 0; $R^5$ is the same as $R^4$ or is an alkyl chain wherein the total number of carbon atoms of $R^2$ plus $R^5$ is from about 8 to about 16; each y averages from 0 to about 10 and the sum of the y values is from 0 to about 15; and X is any compatible anion;

(ii) amine surfactants having the formula:

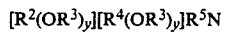

wherein $R^2$, $R^3$, $R^4$, $R^5$ and y are as defined above;

(iii) amine oxide surfactants having the formula:

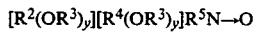

wherein $R^2$, $R^3$, $R^4$, $R^5$ and y are as defined above;

(iv) an amide surfactant of the formula:

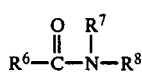

wherein $R^6$ is an alkyl, hydroxyalkyl or alkenyl radical containing from about 8 to about 20 carbon atoms, and $R^7$ and $R^8$ are each selected from the group consisting of hydrogen, methyl, ethyl, propyl, isopropyl, 2-hydroxyethyl, 2-hydroxypropyl, 3-hydroxypropyl, and wherein said radicals additionally contain up to about 5 ethylene oxide units; and (v) mixtures thereof;

(d) from about 5% to about 30% of detergent builder;

(e) a neutralization system;

(f) an aqueous solvent system;

(g) from about 0.1% to about 5.0% of anionic oligomeric soil release esters having the formula

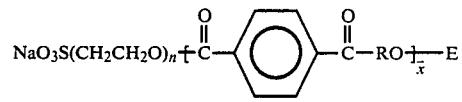

wherein all R substituents are independently selected from —CH$_2$CH$_2$—, —CH$_2$CH(CH$_3$)— and —CH(CH$_3$)CH$_2$—, n is an integer from 2 to 15 or is a number from 2 to 15 representing an average degree of ethoxylation, $\bar{x}$ is the average degree of polymerization of the ester backbone

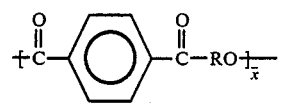

and is a number between 0.3 and 7; and E is a mixture of the substituents

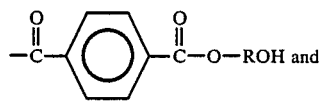

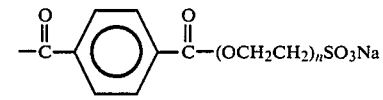

provided that at least 0.5 mole fraction of said E substituents are

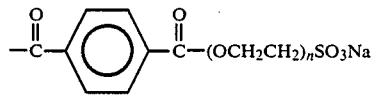

substituents and further provided that at least 0.1 mole fraction of the total of all R substituents are 1,2-propylene substituents.

18. A detergent composition according to claim 17 comprising anionic oligomeric soil release esters wherein at least 0.95 mole fraction of the E substituents are

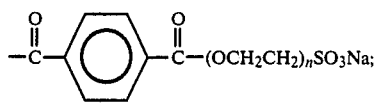

wherein the average degree of ethoxylation, n, is greater than 2; wherein the average degree of polymerization of the ester backbone, $\bar{x}$, is at least about 1.75; and wherein at least 0.33 mole fraction of the total of all R substituents are 1,2-propylene substituents.

* * * * *